United States Patent
Liang

(10) Patent No.: US 11,377,490 B2
(45) Date of Patent: Jul. 5, 2022

(54) METHOD FOR TREATING CANCER USING DISULFIDE-LINKED TRIMERIC 4-1BBL

(71) Applicant: Sichuan Clover Biopharmaceuticals, Inc., Chengdu (CN)

(72) Inventor: Peng Liang, Nashville, TN (US)

(73) Assignee: Sichuan Clover Biopharmaceuticals, Inc, Chengdu (CN)

( * ) Notice: Subject to any disclaimer, the term of this patent is extended or adjusted under 35 U.S.C. 154(b) by 224 days.

(21) Appl. No.: 16/803,126

(22) Filed: Feb. 27, 2020

(65) Prior Publication Data

US 2020/0190181 A1  Jun. 18, 2020

Related U.S. Application Data

(63) Continuation-in-part of application No. 15/609,612, filed on May 31, 2017, now Pat. No. 10,618,949.

(51) Int. Cl.
| | |
|---|---|
| A61K 38/17 | (2006.01) |
| C07K 16/24 | (2006.01) |
| A61K 9/00 | (2006.01) |
| C07K 14/52 | (2006.01) |
| C07K 16/28 | (2006.01) |
| A61K 38/19 | (2006.01) |
| A61P 35/04 | (2006.01) |
| A61K 38/00 | (2006.01) |
| A61K 39/00 | (2006.01) |

(52) U.S. Cl.
CPC .......... *C07K 16/241* (2013.01); *A61K 9/0019* (2013.01); *A61K 38/191* (2013.01); *C07K 14/52* (2013.01); *C07K 16/2818* (2013.01); *C07K 16/2827* (2013.01); *A61K 38/00* (2013.01); *A61K 39/001129* (2018.08); *A61P 35/04* (2018.01); *C07K 2319/00* (2013.01)

(58) Field of Classification Search
None
See application file for complete search history.

(56) References Cited

U.S. PATENT DOCUMENTS

| | | |
|---|---|---|
| 5,605,690 A | 2/1997 | Jacobs et al. |
| 6,190,886 B1 | 2/2001 | Hoppe et al. |
| 6,277,600 B1 | 8/2001 | Tomita et al. |
| 7,268,116 B2 | 9/2007 | Liang |

(Continued)

FOREIGN PATENT DOCUMENTS

| | | |
|---|---|---|
| CA | 2237900 A1 | 5/1997 |
| CA | 2230556 C | 6/2011 |

(Continued)

OTHER PUBLICATIONS

Wei et al., Dual targeting of CD137 co-stimulatory and PD-1 co-inhibitory molecules for ovarian cancer immunotherapy, Concoimmunol. 3:e28248; http://dx.doi.org/10.4161/onci.28248, 3 pages, 2014.*

(Continued)

*Primary Examiner* — Claire Kaufman
(74) *Attorney, Agent, or Firm* — Yuqin Jin

(57) ABSTRACT

Compositions of TNF family of cytokines in covalently linked trimeric forms are disclosed. The resulting fusion proteins are secreted as disulfide bond-linked homotrimers, which are more stable in structure and therapeutically more efficacious than their native counterparts.

17 Claims, 19 Drawing Sheets
Specification includes a Sequence Listing.

(56) References Cited

U.S. PATENT DOCUMENTS

| | | | |
|---|---|---|---|
| 7,691,815 | B2 | 4/2010 | Liang |
| 7,666,837 | B2 | 10/2010 | Liang |
| 10,618,949 | B2 | 4/2020 | Liang |
| 2003/0143564 | A1 | 7/2003 | Burgeson et al. |
| 2003/0148466 | A1 | 8/2003 | Fox et al. |
| 2004/0197876 | A1 | 10/2004 | Tschopp et al. |
| 2005/0202537 | A1 | 9/2005 | Liang |
| 2007/0087413 | A1 | 4/2007 | Liang |
| 2007/0117755 | A1 | 5/2007 | Liang |
| 2015/0126710 | A1* | 5/2015 | Hill ................... A61P 3/00 530/351 |
| 2018/0346549 | A1 | 12/2018 | Liang |
| 2020/0199187 | A1 | 6/2020 | Liang |

FOREIGN PATENT DOCUMENTS

| | | | |
|---|---|---|---|
| CN | 101146818 | | 3/2008 |
| EP | 1671097 | | 8/2013 |
| FR | 2757874 | B1 | 4/2003 |
| JP | 2000-125872 | | 5/2000 |
| WO | WO 1997/017988 | | 5/1997 |
| WO | WO 1998/027202 | | 6/1998 |
| WO | WO 2005/047850 | | 5/2005 |
| WO | WO-2016029043 A1 * | 2/2016 | ........ A61P 35/02 |

OTHER PUBLICATIONS

Rabu et al., Production of recombinant human trimeric CD137L (4-1BBL), J. Biol. Chem. 280(50):41472-41481, Dec. 2005.*

Kelley, S. K. et al. Preclinical studies to predict the disposition of Apo2L/Tumor necrosis factor-related apoptosis-inducing ligand in humans: characterization of in vivo efficacy, pharmacokinetics, and safety. JPET 299, 31-38 (2001).

Wang, S. and El-Deiry, W, S. TRAIL and apoptosis induction by TNF-family death receptors Oncogene 22, 8628-8633 (2003).

Soria, J. C. et al. Phase 1b study of dulanermin (recombinant human Apo2L/TRAIL) in combination with paclitaxel, carboplatin, and bevacizumab in patients with advanced non-squamous non-small-cell lung cancer. J Clin Oncol. 28, 1527-1533(2010).

Soria, J. C. et al. Randomized phase II study of dulanermin in combination with paclitaxel, carboplatin, and bevacizumab in advanced non-small-cell lung cancer. J Clin Oncol. 29, 4442-4451, (2011).

D De Miguel, et al. Onto better TRAILS for cancer treatment. Cell Death Differ. 23, 733-747, (2016).

Biospace, Clover Biopharmaceuticals doses first patient in phase I study of SCB-313 in China for malignant ascites, [Retrieved on line <URL:www.biospace.com/article/releases/clover-biopharmaceuticals-doses-first-patient-in-phase-i-study-of-scb-313-in-china-for-malignant-ascites/>] on Oct. 15, 2021, Sep. 29, 2019.

Chen et al., "A Chimeric Protein of Simian Immunodeficiency Virus Envelope Glycoprotein gp140 and *Escherichia coli* Aspartate Transcarbamoylase" J Virol.(2004) 78:4508-4516.

ClinicalTrails.gov NCT03869697(v1), [Retrieved on line <URL:https://clinicaltrials.gov/ct2/history/NCT03869697?V_1=View#StudyPageTop>] on Oct. 15, 2021, Mar. 7, 2019.

ClinicalTrails.gov NCT04123886(v2), [Retrieved on line KURL:https://clinicaltrials.gov/ct2/history/NCT041238867V_2=View#StudyPageTop>] on Oct. 15, 2021, Oct. 10, 2019.

Frank et al., "Stabilization of Short Collagen-like Triple Helices by Protein Engineering," J. Mol. Biol. (2001) 308:1081-1089.

Grantome Database, Trimer-tag: a technology for producing trivalent biologies, Retrieved online from <URL:http://grantome.com/grant/NIH/R43-AI091286-01A1>. Retrieved on Nov. 25, 2019. 2015.

Haas et al., "Novel intrapleural therapies for malignant diseases," Respiration. (2012) 83(4): 277-92.

Hendriks et al., "Programmed Death Ligand 1 (PD-L1)-targeted TRAIL combines PD-L1-mediated checkpoint inhibition with TRAIL-mediated apoptosis induction," Oncoimmunology. (2016) 5(8): e1202390.

Kim et al., "Death induction by recombinant native TRAIL and its prevention by a caspase 9 inhibitor in primary human esophageal epithelial cells," J Biol Chem. (2004) 279(38): 40044-52.

Mohler et al., "Soluble Tumor Necrosis Factor (TNF) Receptors are Effective Therapeutic Aents in Lethal Endotoxemia and Function Simultaneously as Both TNF Carriers and TNF Antagonists," J. of Immunology, vol. 151, No. 3, p. 1548-1561, 1993.

Sage, E., "Cell Therapy for the Treatnent of Malignant Pleural Mesothelioma," Doctoral thesis, UCL (University College London). (2013), 189 pages.

Spitzer et al., "A genetically encoded multifunctional TRAIL trimer facilitates cellspecific targeting and tumor cell killing," Mol Cancer Ther. (2010) (7): 2142-51.

Wang et al., "Immunoglobulin Fc domain fusion to TRAIL significantly prolongs its plasma half-life and enhances its antitumor activity," Mol Cancer Ther. (2014) 13(3): 643-50.

Yang et al."Characterization of Stable, Soluble Trimers Containing Complete Ectodomains of Human Immunodeficiency Virus Type I Envelope Glycoproteins" J.Virol. K2000) 74:5716-5725.

* cited by examiner

10 mg/kg

80 mg/kg

METHOD FOR TREATING CANCER USING DISULFIDE-LINKED TRIMERIC 4-1BBL

CROSS-REFERENCE TO RELATED APPLICATIONS

This application is a continuation-in-part of U.S. patent application Ser. No. 15/609,612, filed May 31, 2017, and issued as U.S. Pat. No. 10,618,949, the disclosures of which is incorporated by reference in their entireties for all purposes.

INCORPORATION BY REFERENCE OF SEQUENCE LISTING

The present application is being filed along with a Sequence Listing in electronic format. The Sequence Listing is provided as a file entitled Trail-Trimer-Seq-IDs1-7_ST25.txt, created Feb. 27, 2020, which is 28604 bytes in size. The information in the electronic format of the Sequence Listing is incorporated by reference in its entirety.

FIELD OF THE INVENTION

The present invention relates to methods for protein expression, and more specifically, for creating and expressing secreted, disulfide-linked and biologically active trimeric proteins from TNF family of cytokines.

BACKGROUND OF INVENTION

In multicellular organisms, such as mammals, cells communicate with each other by signal transduction pathways, in which a secreted ligand (e.g. cytokines, growth factors, or hormones) binds to its cell surface receptor(s), leading to receptor activation. The receptors are membrane proteins, which consist of an extracellular domain responsible for ligand binding, a central transmembrane region followed by a cytoplasmic domain responsible for sending the signal downstream. Signal transduction can take place in the following three ways: paracrine (communication between neighboring cells), autocrine (cell communication to itself) and endocrine (communication between distant cells through circulation), depending on the source of a secreted signal and the location of target cell expressing a receptor(s). One of the general mechanisms underlying receptor activation, which sets off a cascade of events beneath the cell membrane including the activation of gene expression, is that a polypeptide ligand such as a cytokine, is present in an oligomeric form, such as a homo-dimer or trimer, which when bound to its monomeric receptor at the cell outer surface, leads to the oligomerization of the receptor. Signal transduction pathways play a key role in normal cell development, differentiation and immune surveillance against cancer, as well as in response to external insults such as bacterial and viral infections. Abnormalities in such signal transduction pathways, in the form of either underactivation (e.g. lack of ligand) or overactivation (e.g. too much ligand), are the underlying causes for pathological conditions and diseases such as arthritis, cancer, AIDS, and diabetes.

One of the current strategies for treating these debilitating diseases involves the use of receptor decoys, such as soluble receptors consisting of only the extracellular ligand-binding domain, to intercept a ligand and thus overcome the overactivation of a receptor. A good example of this strategy is the creation of Enbrel©, a dimeric soluble TNF-α receptor-immunoglobulin (IgG) fusion protein by Immunex, which is now part of Amgen. Anti-TNF-α biologics have now become the standard of care for a host of autoimmune diseases. The TNF family of cytokines is one of the major pro-inflammatory signals produced by the body in response to infection and tissue injury. However, abnormal production of these cytokines, for example, in the absence of infection or tissue injury, has been shown to be one of the underlying causes for diseases such as arthritis and psoriasis. Naturally, a TNF-α receptor is present in monomeric form on the cell surface before binding to its ligand, TNF-α, which exists, in contrast, as a homotrimer. Accordingly, fusing a soluble TNF-α receptor with the Fc region of immunoglobulin G1, which is capable of spontaneous dimerization via disulfide bonds, allowed the secretion of a dimeric soluble TNF-α receptor. In comparison with the monomeric soluble receptor, the dimeric TNF-α receptor II-Fc fusion has a greatly increased affinity to the homotrimeric ligand. This provides a molecular basis for its clinical use in treating rheumatoid arthritis (RA), an autoimmune disease in which constitutively elevated TNF-α, a major pro-inflammatory cytokine, plays an important causal role.

In contrast, abnormalities in the production of certain TNF family of cytokines seems to be linked to failure in immune surveillance against cancer. In fact the founding member, TNF-α was initially identified as a cancer cell killer and so named as TNF (tumor necrosis factor). Now, it is known that several members of TNF family of cytokines, including TNF-α, FasL and TRAIL/Apo2L, have the ability to potently elicit cancer cell killing via either apoptosis or necrosis. However, it turns out that overexpression of TNF-α, FasL are toxic to mammals as they elicit potent inflammatory responses. So far only TRAIL/Apo2L retains the characteristics for being cancer-specific killer via apoptosis and has been extensively studied as an anti-cancer biologics (Wang and El-Deiry, 2003). Recombinant TRAIL/Apo2L (Dulanermin/AMG 951) produced from E. coli by Amgen and Genentech showed promising results in preclinical xenograft animal models (Kelley et al., 2001) as well as in Phase I clinical trials against multiple cancers (Soria et al., 2010). However, it failed in several Phase II trials due to lack of efficacy albeit good safety profile (Soria et al., 2011). The lack of efficacy has been linked to Dulanermin's poor pharmacokinetic profile, with very short systemic half-life in mammals; this is likely due to its small molecular weight (~60 kDa) and the instability of its non-covalently linked trimeric structure, both ultimately leading to its rapid elimination via renal filtration (Kelley et al., 2001). Thus, trimerization via covalent bond linkage may stabilize TRAIL/Apo2L trimeric structure essential for its biological activity as well as to increase the molecular weight to extend half-life for improved efficacy.

Although there have been various approaches to overcoming such challenges faced by native TRAIL (de Miguel et al. 2016), such attempts have ultimately fallen short as feasible human therapies. A leucine zipper fused TRAIL and a cross-linked TRAIL stabilized by inserted mutations creating an additional artificial disulfide bond are both potentially immunogenic in humans due to the non-human nature of their added oligomerization domains; moreover, both have demonstrated hepatotoxicity not observed with native TRAIL. Other methods for extending half-life of TRAIL have also encountered obstacles; albumin conjugated TRAIL nanoparticles must be prepared in organic solvents and production was extremely limited. Similar production issues are faced by liposome conjugated TRAIL.

Recently, immuno-oncology as a paradigm for cancer therapy has made great progress with the approvals of therapeutic antibodies against PD-1, PD-L1 and CTLA-4, with exciting sustained remissions for certain cancer patients, including melanoma. Programmed cell death protein 1, also known as PD-1, is a cell surface receptor that belongs to the immunoglobulin superfamily and is expressed on T cells and pro-B cells. PD-1 binds two ligands, PD-L1 and PD-L2. PD-1 is a member of the extended CD28/CTLA-4 family of T cell regulators. PD-1 and its ligands play an important role in downregulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen-specific T cells in lymph nodes while simultaneously reducing apoptosis in regulatory T cells (suppressor T cells). Therapeutic antibodies that block PD-1 or its ligand (PD-L1) as well as CTLA-4, activate the immune system to attack tumors and are therefore used to treat cancer. These breakthroughs demonstrated that cancer is an immune disease with cancer cells evading the body's immune surveillance by inhibiting several key immune check-points such as PD-1 and CTLA-4 signaling pathways. Importantly, there is an increasing body of evidence showing that several members of TNF family of cytokines, such as 4-1BBL (also called CD137L) and OX40L, can potently stimulate proliferation and survival of antigen-specific cytotoxic T cells as well as stimulate the memory T cell response. Thus, combinational use of PD-1 or CTLA-4 antagonists with 4-1BB or OX40 agonists may fully activate the body's immune attack against cancer. Like all members of TNF family of cytokines, 4-1BBL and OX40L are small in molecular weight and homo-trimeric in structure without inter-subunit disulfide bond linkages.

Clearly, there is a great need to be able to create secreted homo-trimeric and disulfide bond-strengthened TNF family of cytokines that retain full biological activities. Compared to their native counterparts produced from bacteria, such rationally designed TNF family of ligand-Trimers produced in mammalian cells such as CHO cells, may significantly increase the efficacy for cancer treatment. To be therapeutically feasible, a desired trimerizing protein moiety for biologic drug designs should satisfy the following criteria. Ideally it should be part of a naturally secreted protein, like immunoglobulin Fc, that is also abundant (non-toxic) in the circulation, human in origin (lack of immunogenicity), relatively stable (long half-life) and capable of efficient self-trimerization which is strengthened by interchain covalent disulfide bonds, so the trimerized TNF family of cytokines are structurally stable.

Collagen is a family of fibrous proteins that are the major components of the extracellular matrix. It is the most abundant protein in mammals, constituting nearly 25% of the total protein in the body. Collagen plays a major structural role in the formation of bone, tendon, skin, cornea, cartilage, blood vessels, and teeth. The fibrillar types of collagen I, II, III, IV, V, and XI are all synthesized as larger trimeric precursors, called procollagens, in which the central uninterrupted triple-helical domain consisting of hundreds of "G-X-Y" repeats (or glycine repeats) is flanked by non-collagenous domains (NC), the N-propeptide and the C-propeptide. Both the C- and N-terminal extensions are processed proteolytically upon secretion of the procollagen, an event that triggers the assembly of the mature protein into collagen fibrils which forms an insoluble cell matrix. BMP-1 is a protease that recognizes a specific peptide sequence of procollagen near the junction between the glycine repeats and the C-prodomain of collagens and is responsible for the removal of the propeptide. The shed trimeric C-propeptide of type I collagen is found in human sera of normal adults at a concentration in the range of 50-300 ng/mL, with children having a much higher level which is indicative of active bone formation. In people with familial high serum concentration of C-propeptide of type I collagen, the level could reach as high as 1-6 µg/mL with no apparent abnormality, suggesting the C-propeptide is not toxic. Structural study of the trimeric C-propeptide of collagen suggested that it is a tri-lobed structure with all three subunits coming together in a junction region near their N-termini to connect to the rest of the procollagen molecule. Such geometry in projecting proteins to be fused in one direction is similar to that of Fc dimer.

Type I, IV, V and XI collagens are mainly assembled into heterotrimeric forms consisting of either two α-1 chains and one α-2 chain (for Type I, IV, V), or three different a chains (for Type XI), which are highly homologous in sequence. The type II and III collagens are both homotrimers of α-1 chain. For type I collagen, the most abundant form of collagen, stable α1(I) homotrimer is also formed and is present at variable levels in different tissues. Most of these collagen C-propeptide chains can self-assemble into homotrimers, when over-expressed alone in a cell. Although the N-propeptide domains are synthesized first, molecular assembly into trimeric collagen begins with the in-register association of the C-propeptides. It is believed the C-propeptide complex is stabilized by the formation of interchain disulfide bonds, but the necessity of disulfide bond formation for proper chain registration is not clear. The triple helix of the glycine repeats and is then propagated from the associated C-termini to the N-termini in a zipper-like manner. This knowledge has led to the creation of non-natural types of collagen matrix by swapping the C-propeptides of different collagen chains using recombinant DNA technology. Non-collagenous proteins, such as cytokines and growth factors, also have been fused to the N-termini of either procollagens or mature collagens to allow new collagen matrix formation, which is intended to allow slow release of the noncollagenous proteins from the cell matrix. However, under both circumstances, the C-propeptides are required to be cleaved before recombinant collagen fibril assembly into an insoluble cell matrix.

Although, other protein trimerization domains, such as those from GCN4 from yeast fibritin from bacteria phage T4 and aspartate transcarbamoylase of *Escherichia coli*, have been described previously to allow trimerization of heterologous proteins, none of these trimerizing proteins are human in nature, nor are they naturally secreted proteins. As such, any trimeric fusion proteins would have to be made intracellularly, which not only may fold incorrectly for naturally secreted proteins such as soluble receptors, but also make purification of such fusion proteins from thousands of other intracellular proteins difficult. Moreover, the fatal drawback of using such non-human protein trimerization domains (e.g., from yeast, bacteria phage and bacteria) for trimeric biologic drug design is their presumed immunogenicity in the human body, rendering such fusion proteins ineffective shortly after injecting them into the human body.

One secreted protein previously used as a protein trimerization tag is tetranectin, which is a plasminogen-binding protein of C-lectin family. However, unlike IgG Fc dimerization tag, the trimeric tetranectin structure is not strengthened by any interchain disulfide bonds, and significant fractions of both monomeric and dimeric tetranectin co-existed with the trimeric structure in solution. Physiologically, teranectin is involved in tissue remodeling and increased cell matrix concentration of tetranectin in human has been linked to multiple cancer types. Recombinant heterologous tetranectin fusion proteins have only been produced intracellularly in *E. coli* as insoluble inclusion bodies that required refolding to obtain soluble structures. These unfavorable attributes suggest that tetranectin is not ideal for therapeutic applications as a protein trimerization tag. Nonetheless, bacterially produced ApoAI-Tetranectin fusion protein has been produced and patented and is being tested as a therapeutic agent for atherosclerosis.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

Disclosed here is an invention that allows any TNF family of cytokines (ligands) to be made into disulfide bond-linked trimeric forms as secreted proteins. The essence of the invention is to fuse a signal peptide in-frame to any the N-terminus of a soluble TNF family of cytokines, which in turn is fused in-frame to the C-propeptide domain of a collagen, which is capable of self-trimerization, using recombinant DNA technology or via total gene synthesis. The resulting DNA construct encoding such fusion proteins when expressed in eukaryotic cells are secreted as soluble proteins essentially 100% in trimeric forms covalently strengthened by inter-molecular disulfide bonds formed among three C-propeptides. The resulting trimeric TNF family of cytokines are fully active and can be purified for therapeutic applications.

In one aspect of the invention, a secreted fusion protein comprises a soluble ligand from TNF family of cytokines joined by in-frame fusion to a C-terminal portion of collagen which is capable of self-trimerization to form a disulfide bond-linked trimeric fusion protein. In another aspect of the invention, a secreted fusion protein disclosed above, wherein the soluble ligand from TNF family of cytokines is selected from the group consisting of TRAIL, TNF-α, 41BBL, OX40L, GITRL, HVEML, CD27L, CD30L, RANKL, BLyS, CD40L, DR3L and APRIL.

In one aspect of the invention, a secreted TNF family of trimeric fusion protein wherein the C-terminal portion of collagen is selected from the group consisting of pro.alpha.1 (I), pro.alpha. 2(I), pro.alpha.1(II), pro.alpha.1(111), pro.alpha.1(V), pro.alpha.2(V), pro.alpha.1(XI), pro.alpha.2(XI) and pro.alpha.3(XI). In one aspect of the invention, a secreted TNF family of trimeric fusion protein wherein the C-terminal portion of collagen further comprises a C-propeptide without any glycine-repeat triple helical regions of collagen. In one aspect of the invention, a secreted TNF family of trimeric fusion protein wherein the C-terminal portion of collagen further comprises a glycine-repeat triple helical region of collagen linked to a C-propeptide. In one aspect of the invention, a secreted TNF family of trimeric fusion protein wherein the C-terminal portion of collagen further comprises a mutated or deleted BMP-1 protease recognition sequence.

In a preferred embodiment, the secreted fusion protein, wherein the soluble ligand from TNF family of cytokines is TRAIL, and the C-terminal portion of collagen of pro.alpha.1(I) comprises a mutated BMP-1 protease recognition sequence comprising the amino acid sequences set forth in either SEQ ID NO: 1 or SEQ ID NO: 2.

In another preferred embodiment, the secreted fusion protein, wherein the soluble ligand from TNF family of cytokines is 4-1BBL, and the C-terminal portion of collagen comprises pro.alpha.1(I) with a mutated BMP-1 protease recognition sequence comprising the amino acid sequences set forth in either SEQ ID NO: 3 or SEQ ID NO: 4.

In yet another preferred embodiment, the secreted fusion protein, wherein the soluble ligand from TNF family of cytokines is OX40L, and the C-terminal portion of collagen comprises pro.alpha.1(I) with a deleted BMP-1 protease recognition sequence comprising the amino acid sequences set forth in either SEQ ID NO: 5 or SEQ ID NO: 6.

In one embodiment, the secreted fusion protein, wherein the soluble ligand from TNF family of cytokines is TNF-α, and the C-terminal portion of collagen comprises pro.alpha.1(I) with a mutated BMP-1 protease recognition sequence comprising the amino acid sequence set forth in SEQ ID NO: 7.

In one aspect of the invention, a method for treating cancer in a mammal comprises administering to said mammal a therapeutically effective amount of a disulfide bond-linked trimeric TRAIL fusion protein comprising the amino acid sequences set forth in either SEQ ID NO: 1 or SEQ ID NO: 2.

In a preferred embodiment, a method for treating cancer in a mammal, wherein the cancer is gastrointestinal cancer including those from colorectal, gastric, esophageal and pancreatic origins, comprises administering to said mammal a therapeutically effective amount of a disulfide bond-linked trimeric TRAIL fusion protein. In another preferred embodiment, a method for treating cancer in a mammal, wherein the cancer is malignant ascites, comprises administering to said mammal a therapeutically effective amount of a disulfide bond-linked trimeric TRAIL fusion protein. In varying embodiments, the various compositions taught in the present invention may be used to treat any type of cancer. Additional examples of cancers that may be treated include, but are not limited to: lung cancer, pancreatic cancer, ovarian cancer, malignant ascites, and peritoneal carcinomatosis.

In one aspect of the invention, a method for treating cancer in a mammal comprises administering to said mammal a therapeutically effective amount of anti-PD1, anti-PD-L1 or anti-CTLA-4 plus a disulfide bond-linked trimeric 4-1BBL fusion protein with amino acid sequences set forth in either SEQ ID NO: 3 or SEQ ID NO: 4.

In yet another aspect of the invention, a method for treating cancer in a mammal comprises administering to said mammal a therapeutically effective amount of anti-PD1, anti-PD-L1 or anti-CTLA-4 plus a disulfide bond-linked trimeric OX40L fusion protein with an amino acid sequence set forth in either SEQ ID NO: 5 or SEQ ID NO: 6.

In one aspect of the invention, a method for treating cancer in a mammal comprises administering to said mammal a therapeutically effective amount the disulfide bond-linked trimeric fusion protein via either intravenous injection, intraperitoneal infusion or subcutaneous injection.

In another aspect of the invention, a method for treating cancer in a mammal comprises administering to said mammal a therapeutically effective amount of the disulfide bond-linked trimeric fusion protein in a series of doses separated by intervals of days or weeks.

In one aspect of the invention, a method for treating cancer in a mammal comprises administering to said mammal a therapeutically effective amount of the disulfide bond-linked trimeric fusion protein in combination with chemotherapy or inhibitors that blocks Ras signaling pathways.

In a preferred embodiment, a method for treating cancer in a mammal comprises administering to said mammal a therapeutically effective amount of TRAIL-Trimer in combination with Sulindac which inhibits NFkB pathway which is downstream of Ras.

In another preferred embodiment, a method for treating cancer in a mammal comprises administering to said mammal a therapeutically effective amount of TRAIL-Trimer in combination with an EGFR inhibitor, such as Iressa.

In another aspect of the invention, a method for treating malignant ascites in a mammal comprises administering to said mammal via intraperitoneal injection/infusion a therapeutically effective amount of TRAIL-Trimer or TRAIL.

In another preferred embodiment, a method for treating malignant pleural effusion in a mammal comprises administering to said mammal via intra-pleural injection/infusion a therapeutically effective amount of TRAIL-Trimer or TRAIL.

In yet another aspect of the invention, a method for treating cancer in a mammal comprises administering to said mammal with TRAIL-Trimer which induces cancer cell-specific apoptosis (tumor antigen release), in combination with immune checkpoint inhibitors such as anti-PD-1 or anti-PD-L1 to more efficiently contain the tumor in a long lasting basis.

The following are the advantages of this invention: (1) collagen is the most abundant protein secreted in the body of a mammal, constituting nearly 25% of the total proteins in the body; (2) the major forms of collagen naturally occur as trimeric helixes, with their globular C-propeptides being responsible for the initiating of trimerization; (3) the trimeric C-propeptide of collagen proteolytically released from the mature collagen is found naturally at sub microgram/mL level in the blood of mammals and is not known to be toxic to the body; (4) the linear triple helical region of collagen can be included as a linker with predicted 2.9 Å spacing per residue, or excluded as part of the fusion protein so the distance between a protein to be trimerized and the C-propeptide of collagen can be precisely adjusted to achieve an optimal biological activity; (5) the recognition site of BMP1 which cleaves the C-propeptide off the pro-collagen can be mutated or deleted to prevent the disruption of a trimeric fusion protein; (6) the C-propeptide domain self-trimerizes via disulfide bonds and it provides a universal affinity tag, which can be used for purification of any secreted fusion proteins created by this invention.

In contrast to any TNF family of cytokines such as TRAIL, TRAIL-Trimer (designated SCB-313) is covalently linked homo-trimer, thus theoretically more stable than the native and non-covalently bonded trimers such as TRAIL (FIG. 1).

In contrast to the Fc Tag technology, with which secreted dimeric fusion proteins can be created, this timely invention disclosed herein enables the creation and secretion of soluble, disulfide bond-linked trimeric fusion proteins from TNF family of cytokines at high level (FIG. 2 and FIG. 3).

Given the fact that a homotrimer has 3-fold symmetry, whereas a homodimer has only 2-fold symmetry, the two distinct structural forms theoretically can never be perfectly overlaid (FIG. 1). Consistently, we demonstrated that TRAIL-Trimer created by this invention with its amino acid sequence composition set forth in SEQ ID NO: 2 is over 100 times more potent in cancer cell killing (IC50=67 ng/mL) compared to TRAIL-Fc dimer (IC50=6700 ng/mL) (FIG. 1 and FIG. 7).

In addition to structural stability, the trimerized TNF family of fusion cytokines have significantly increased molecular weight (>160 Kda) than their corresponding native cytokines (~60 Kda), thus are predicted and confirmed to have longer half lives in sera due to less leakage through renal filtration when administered into the body (FIG. 8). The high potency of disulfide bond-linked trimeric TNF family of cytokines with extended sera half lives increased the drug exposure to the tumor cells and led to significant improvement in tumor reduction in vivo, compared to native TRAIL (FIG. 9).

Finally, we also discovered that, in contrast to the rapid systemic elimination of native TNF family of cytokines leading to their very short half-lives, both native TRAIL and TRAIL-Trimer showed dramatically longer half-lives in tumor ascites in the intraperitoneal cavity of mice, with $T_{1/2}$ measured in hours instead of minutes compared to that in sera. Since treatment of malignant ascites is still an unmet medical need for many end-stage cancer patients, particularly from gastrointestinal and gynecological cancer origins, TRAIL-Trimer as well as native TRAIL may be used to treat metastatic ascites, given their tumor cell killing efficacy in vivo clearly hinges on their stability and sustained exposure to tumors. To this end we demonstrated that subcutaneous-inoculation of human gastric cancer cell line (SNU-16) isolated from a patient's malignant ascites is very sensitive to TRAIL-Trimer (FIG. 14), and this finding would predict that TRAIL-Trimer and TRAIL may also be used to more effectively treat human malignant ascites caused by tumor cells that have metastasized to the intraperitoneal cavity.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto. These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of embodiments thereof, which description should be considered in conjunction with the accompanying drawings, in which.

Evaluation of 4-1BBL-Trimer dosing regimen and effects on in vivo antitumor activity (Upper Right Panel). C57BL/6 mice homozygous for human hCD137 (4-1BB receptor) knock-in with established mc38 tumor xenografts were administered with vehicle or 4-1BBL-Trimer (15 mg/kg) as an i.v. bolus injection. Two dosing regimens for 4-1BBL-Trimer were explored: 3 doses (on Days 0, 1, 2), or 7 doses (on Days 0, 1, 2, 4, 7, 10, 13), as indicated. Tumor volume results shown are group mean±SEM, with each group consisting of 10 animals.

Figure 14A:
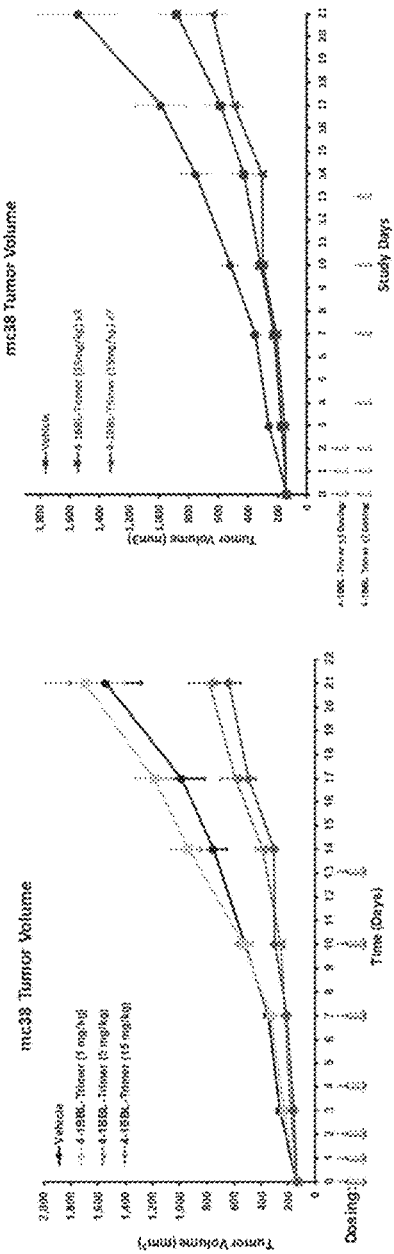
FIG. 14A is in vivo antitumor activity of 4-1BBL-Trimer. C57BL/6 mice homozygous for human hCD137 (4-1BB receptor) knock-in with established mc38 tumor xenografts were administered with vehicle or 4-1BBL-Trimer (1 mg/kg, 5 mg/kg, 15 mg/kg) as i.v. bolus injections as indicated on Days 0, 1, 2, 4, 7, 10, 13 (Upper Left). Tumor volume results shown are group mean±SEM, with each group consisting of 10 animals.
Figure 14B:
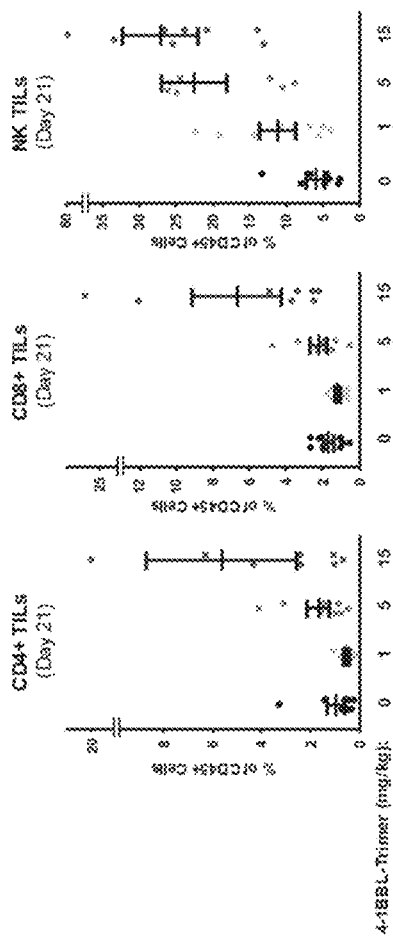

FIG. 14B is FACs analysis of tumor xenografts harvested on Day 21 from FIG. 14A and processed for presence of tumor infiltrating lymphocytes (TILs), including CD4+, CD8+ and NK cells (lower graph).

Figure 15:
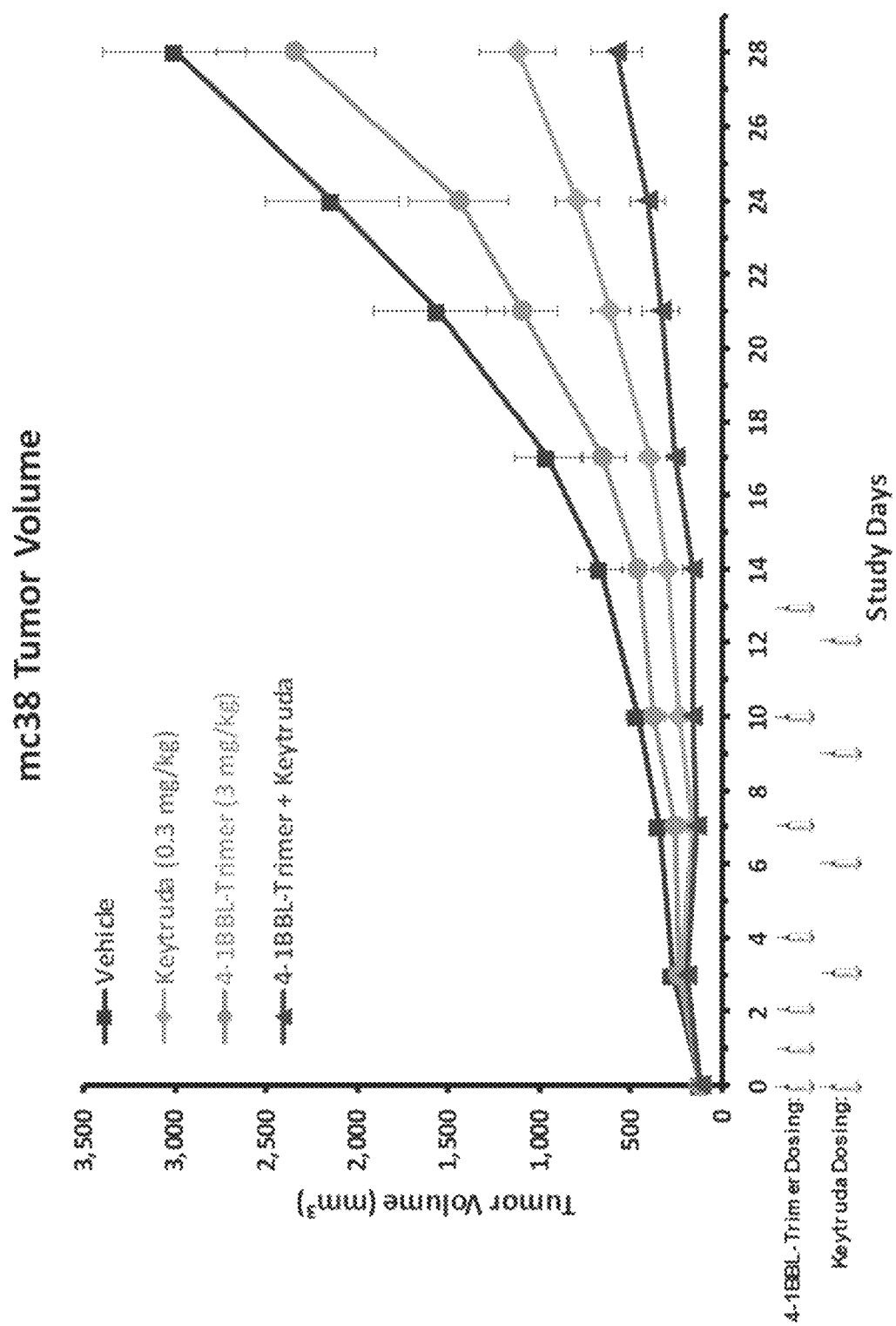

FIG. 15 is evaluation of in vivo antitumor activity of 4-1BBL-Trimer in combination with anti-PD-1 antibody. C57BL/6 mice homozygous for both human hPD-1 knock-in and human hCD137 (4-1BB receptor) knock-in with established mc38 tumor xenografts were administered with vehicle, anti-PD-1 antibody KEYTRUDA® (pembrolizumab) (0.3 mg/kg), 4-1BBL-Trimer (15 mg/kg), or 4-1BBL-Trimer+KEYTRUDA® (pembrolizumab) combination. Tumor volume results shown are group mean±SEM, with each group consisting of 8 animals.

Figure 16:
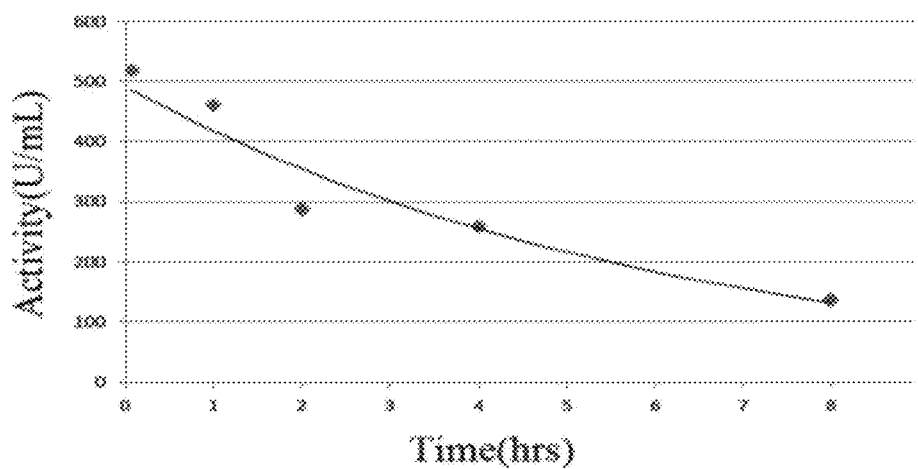
Figure 16:
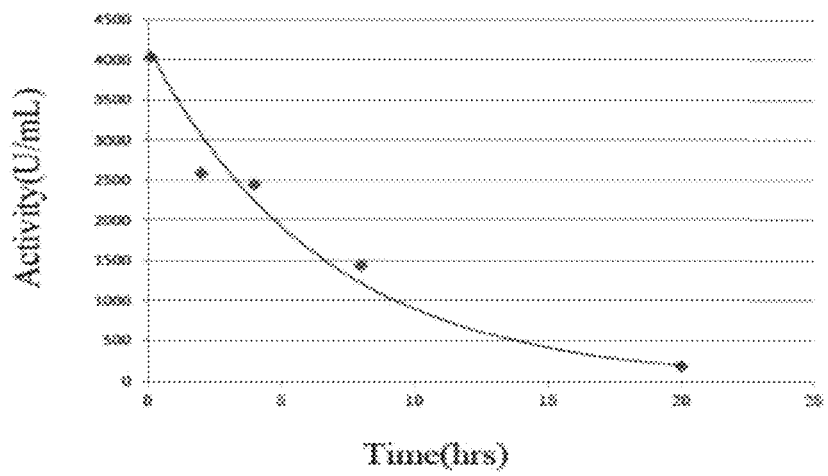

FIG. 16 is PHARMACOKINETIC PROFILE TRAIL-TRIMER IN ASCITES. Balb/c mice with ascites developed via inoculation of a hybridoma cell line unrelated to TRAIL were injected intraperitoneally with either 10 mg/kg (upper panel) or 80 mg/kg (lower panel) of TRAIL-Trimer (n=2 for each dosing). Relative concentration of TRAIL-Trimer was evaluated at periodic intervals using the standard bioassay (colo205 cells) and fluid taken from the ascites. The estimated half-life of TRAIL-Trimer was in the range of 4-5 hrs.

Figure 17:
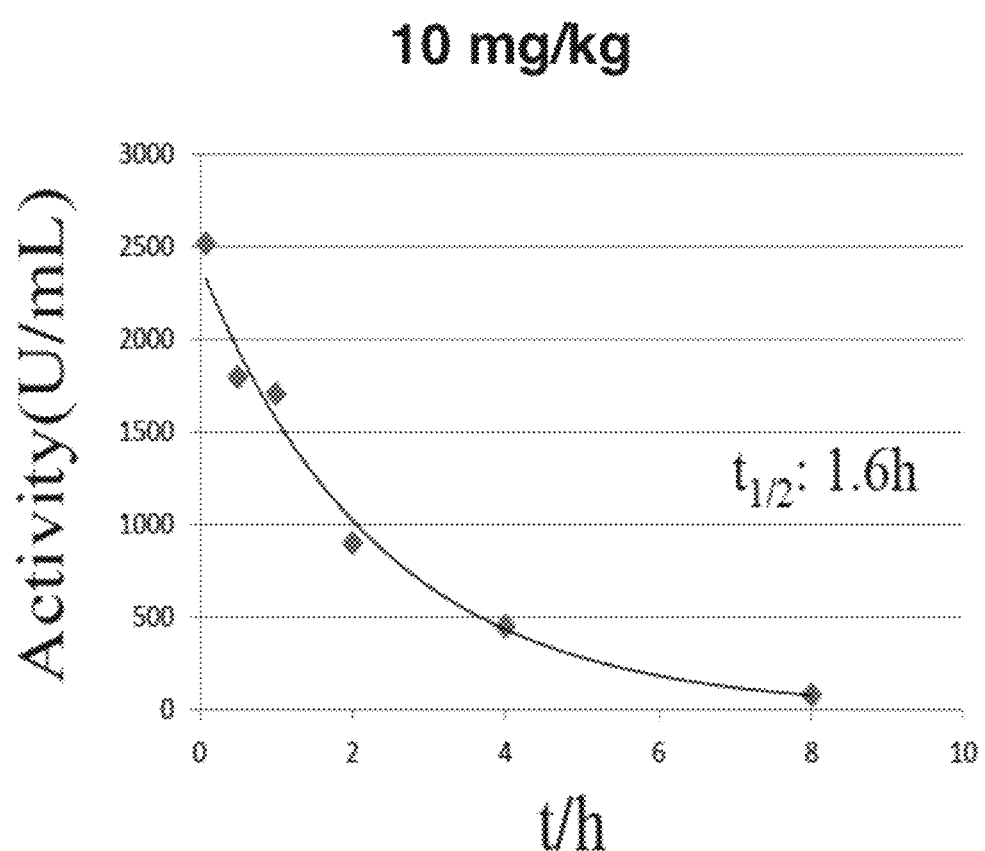

FIG. 17 is PHARMACOKINETIC PROFILE OF NATIVE TRAIL (NTRAIL) IN MOUSE ASCITES. Balb/c mice with ascites developed via inoculation of a hybridoma cell line unrelated to TRAIL were injected intraperitoneally with 10 mg/kg (n=2). Relative concentration of TRAIL-Trimer was evaluated at periodic intervals with fluid taken from the ascites using the standard bioassay (colo205 cells) and Western blot analysis. The estimated half-life of TRAIL was in the range of 2-5 hrs.

Figure 18:
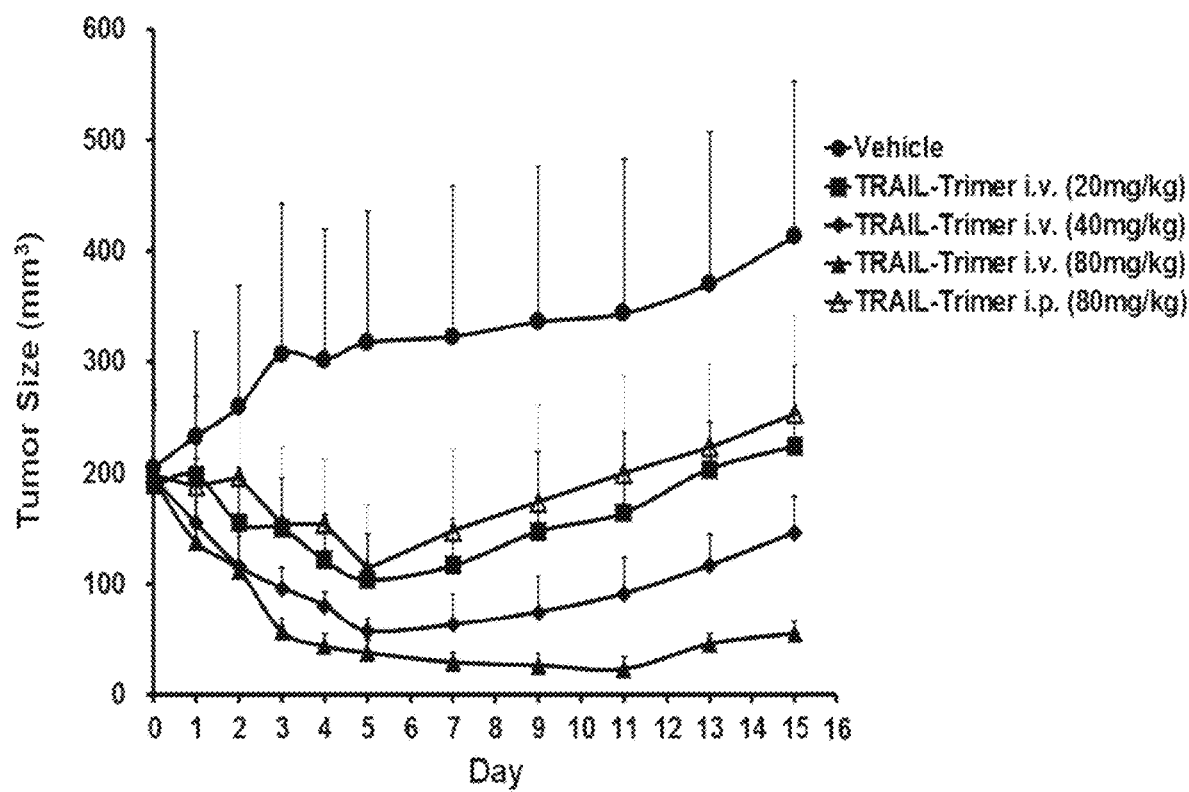

FIG. 18 is the in vivo antitumor activities of TRAIL-Trimer against SNU-16 which is a human gastric cancer cell line established from metastatic ascites. Nude mice with established subcutaneous xenografts of SNU-16 cells were given TRAIL-Trimer (20, 40, or 80 mg/kg/day) or vehicle as an i.v. bolus for 5 consecutive days (n=6/group). As a control, we also delivered TRAIL-Trimer at 80 mg/kg/day for 5 consecutive days via intraperitoneal (i.p.) injections (n=6/group).

Figure 19:
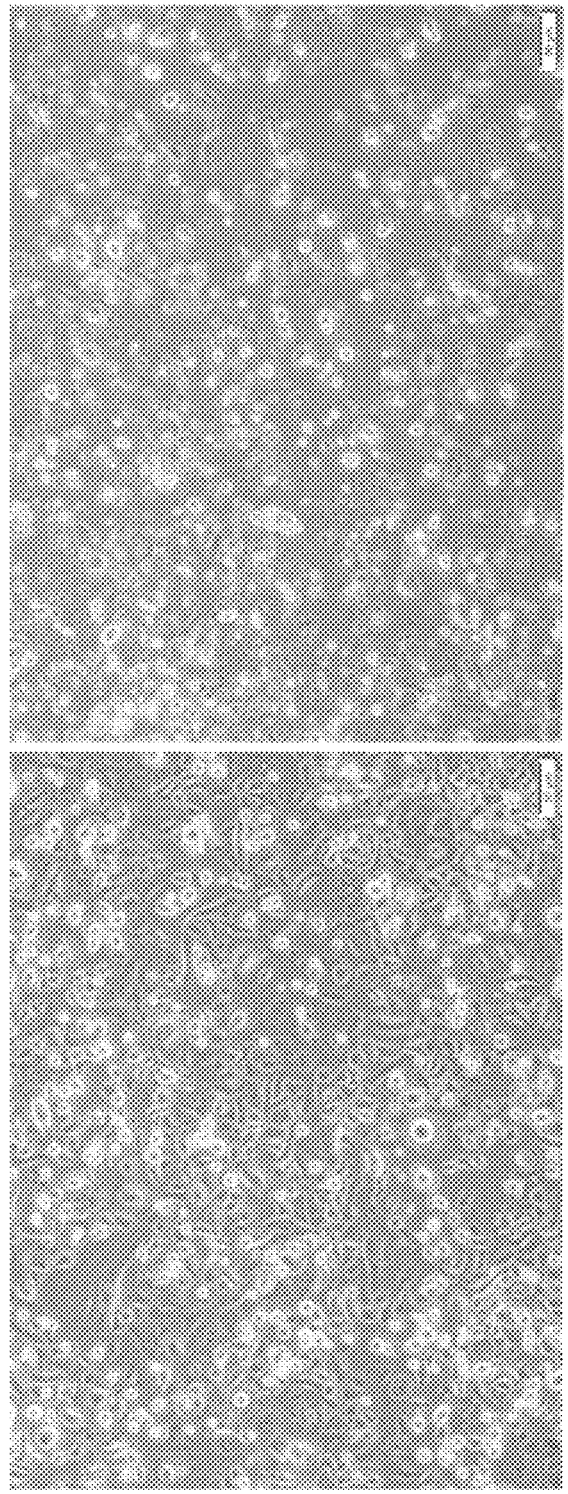

FIG. 19 is in vitro antitumor activity of TRAIL-Trimer against LHA-MPE which is a human pancreatic cancer cell line derived from malignant pleural effusion. LHA-MPE cell line was cultured in RPMI medium with 10% FBS. Twenty four hours after the addition of 1 μg/mL of TRAIL-Trimer, LHA-MPE pancreatic cancer cells essentially all underwent apoptosis (Right Panel), in comparison with cells that were added PBS as a vehicle control (Left Panel).

DESCRIPTION OF SEQUENCE LISTINGS

SEQ ID NO: 1 (479 amino acids): Shows the amino acid sequence for TRAIL-Trimer with native soluble human TRAIL sequence.

SEQ ID NO: 2 (482 amino acids): Shows the amino acid sequence for TRAIL-Trimer (variant 1) with a modified N-terminus of soluble human TRAIL sequence.

SEQ ID NO: 3 (495 amino acids): Shows the amino acid sequence for 4-1BBL-Trimer with native soluble human 4-1BBL sequence.

SEQ ID NO: 4 (498 amino acids): Shows the amino acid sequence for 4-1BBL-Trimer (variant 1) with a modified N-terminus of soluble human 4-1BBL sequence.

SEQ ID NO: 5 (444 amino acids): Shows the amino acid sequence for OX40L-Trimer with native soluble human OX40L sequence.

SEQ ID NO: 6 (447 amino acids): Shows the amino acid sequence for OX40L-Trimer (variant 1) with a modified N-terminus of soluble human OX40L sequence.

SEQ ID NO: 7 (403 amino acids): Shows the amino acid sequence for TNF-α-Trimer with native soluble human TNF-α sequence.

DETAILED DESCRIPTION OF THE EMBODIMENTS

While several variations of the present invention have been illustrated by way of example in particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

Prior to setting forth the invention, it may be helpful to an understanding thereof to set forth definitions of certain terms to be used hereinafter.

DNA Construct: A DNA molecule, generally in the form of a plasmid or viral vector, either single- or double-stranded that has been modified through recombinant DNA technology to contain segments of DNA joined in a manner that as a whole would not otherwise exist in nature. DNA constructs contain the information necessary to direct the expression and/or secretion of the encoding protein of interest.

Signal Peptide Sequence: A stretch of amino acid sequence that acts to direct the secretion of a mature polypeptide or protein from a cell. Signal peptides are characterized by a core of hydrophobic amino acids and are typically found at the amino termini of newly synthesized proteins to be secreted or anchored on the cell surface. The signal peptide is often cleaved from the mature protein during secretion. Such signal peptides contain processing sites that allow cleavage of the signal peptides from the mature proteins as it passes through the protein secretory pathway. A signal peptide sequence when linked to the amino terminus of another protein without a signal peptide can direct the secretion of the fused protein. Most of the secreted proteins, such as growth factors, peptide hormones, cytokines and membrane proteins, such as cell surface receptors, contain a signal peptide sequence when synthesized as a nascent protein.

Soluble receptor: The extracellular domain, in part or as a whole, of a cell surface receptor, which is capable of binding its ligand. Generally, it does not contain any internal stretch of hydrophobic amino acid sequence responsible for membrane anchoring.

C-propeptide of collagens: The C-terminal globular, and non-triple-helical domain of collagens, which is capable of self-assembly into trimers. In contrast to the triple helical region of collagens, the C-propeptide does not contain any glycine repeat sequence and is normally proteolytically removed from procollagen precursor upon procollagen secretion before collagen fibril formation.

Glycine repeats: The central linear triple helix forming region of collagen which contains hundreds of $(Gly-X-Y)_n$ repeats in amino acid sequence. These repeats are also rich in proline at X or/and Y positions. Upon the removal of N- and C-propeptides, the glycine-repeats containing collagen triple helices can assemble into higher order of insoluble collagen fibrils, which make up the main component of the cell matrix. cDNA: Stands for complementary DNA or DNA sequence complementary to messenger RNA. In general cDNA sequences do not contain any intron (non-protein coding) sequences.

One of the modern strategies for treating autoimmune diseases involves the use of biologic TNF antagonists, such as soluble receptors or therapeutic antibodies. However, current TNF-α biologic blockers are all dimeric in structure, whereas TNF-α itself is homotrimeric in nature. Here we describe a general methodology for efficient creation of trimeric soluble receptors. The process involves gene fusion between a soluble receptor with a ligand binding domain and a trimerization tag from the C-propeptide domain of pro-collagen (Trimer-Tag™), which is capable of self-assembly into a covalently linked trimer. Using both in vitro bioassays and an in vivo mouse model for collagen-induced arthritis (CIA), we show that the homotrimeric soluble TNF receptor produced with such method is a more potent blocker than dimeric TNF receptor decoys in inhibiting TNF-α signaling. Thus, Trimer-Tag™ provides a new platform for rational design of the next generation biologic drugs against autoimmune diseases.

Prior to this invention, nearly all therapeutic antibodies and soluble receptor-Fc fusion proteins, such as Enbrel®, are dimeric in structure. Although these molecules, compared to their monomeric counterparts, have been shown to bind their target antigens or ligands with increased avidity, it is predicted that they are still imperfect, due to structural constraints, to bind their targets that have a homotrimeric structure. Examples of such therapeutically important trimeric ligands include TNF family of cytokines. Therefore, from a structural point of view, it will be desirable to be also able to generate trimeric soluble receptors or antibodies, which can perfectly dock to their target trimeric ligands, and thereby completely block the ligand actions.

This invention discloses ways for generating such secreted trimeric receptors and biological active proteins by fusing them to the C-propeptides of collagen, which are capable of self-assembly into trimers. The following are the advantages of this invention: (1) collagen is the most abundant protein secreted in the body of a mammal, constituting nearly 25% of the total protein in the body; (2) the major forms of collagen naturally occur as trimeric helixes, with their globular C-propeptides responsible for the initiating of trimerization, which are subsequently proteolytically cleaved upon triple helix formation; (3) the cleaved soluble trimeric C-propeptide of collagen is found naturally at sub microgram/mL level in the blood of mammals; (4) the linear triple helical region of collagen can be included as a linker or excluded as part of the fusion protein so the distance between a protein to be trimerized and the C-propeptide of collagen can be precisely adjusted to achieve an optimal biological activity; (5) the recognition site of BMP1 which cleaves the C-propeptide off the pro-collagen can be mutated or deleted to prevent the disruption of a trimeric fusion protein; (6) the C-propeptides domain provides a universal affinity tag, which can be used for purification of any secreted fusion proteins created by this invention; (7) unlike the IgG1 Fc tag which is known to be have other biological functions such as binding to its own cell surface receptors, the only known biological function of the C-propeptide of collagen is its ability to initiate trimerization of nascent pro-collagen chains and keep the newly made pro-collagen trimer soluble before assembly into insoluble cell matrix. These unique properties of the C-propeptide of collagen would predict that this unique trimerization tag is unlikely going to be toxic, or immunogenic, making it an ideal candidate for therapeutic applications.

Figure 1:
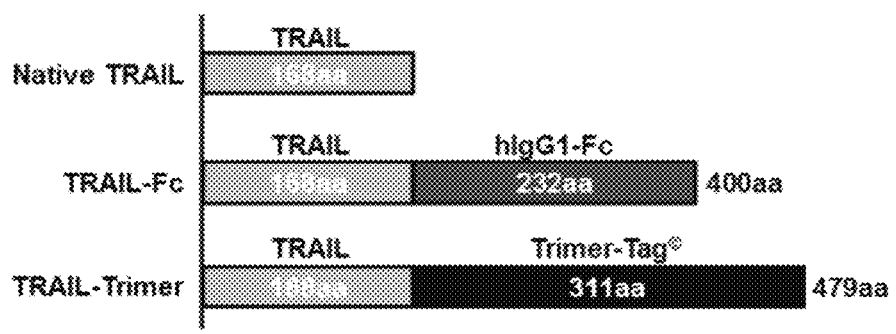
FIG. 1 is schematic representation of structural differences of TRAIL polypeptides used in this study. Upper panel: Three recombinant soluble forms of human TRAIL have been used in this study: a native TRAIL comprised of the extracellular domain of TRAIL, a dimeric TRAIL-Fc comprised of extracellular TRAIL domain fused to human IgG1 Fc domain, and a TRAIL-Trimer comprised of extracellular TRAIL domain fused to the C-prodomain of a Type I collagen (Trimer-Tag™) with a mutated BMP-1 site. Amino acid sequence lengths are shown for each protein and domain respectively. Lower panel: Theoretical molecular weights (kDa) of both monomeric and multimeric forms of native TRAIL, TRAIL-Fc and TRAIL-Trimer, respectively. Native TRAIL associates into a noncovalently-linked homotrimer, TRAIL-Fc forms a covalently-linked homodimer, and TRAIL-Trimer forms a covalently-linked homotrimer.
Figure 1:
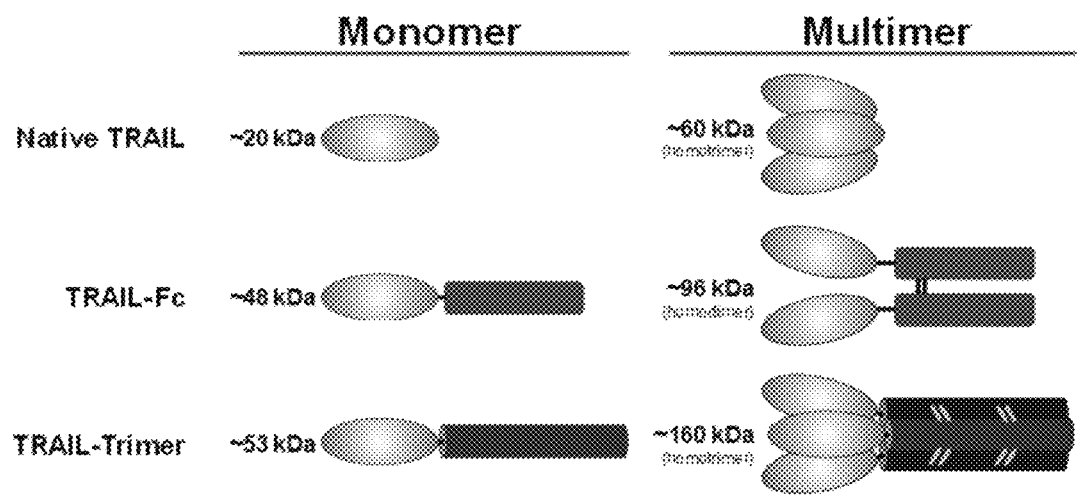

Example 1: Expression, Purification and Functional Characterization of TRAIL-Trimer Thus, trimerization via covalent bond-linkage may stabilize TRAIL/Apo2L trimeric structure essential for its biological activity as well as increase the molecular weight in order to extend half-life for improved antitumor efficacy in vivo. In this study, we show that in-frame fusion of human C-propeptide of α1(I) collagen (dubbed Trimer-Tag™) to the C-terminus of mature human TRAIL leads to a disulfide bond-linked homotrimer (FIG. 1). TRAIL-Trimer (designated SCB-313) was encoded by cDNA a sequence with the following coding sequences fused in tandem: Promoter-Signal peptide-Mature TRAIL-"Trimer-Tag™". The cDNA sequence encoding the mature human TRAIL (aa 114-281 of full length human TRAIL protein) was either PCR amplified or gene synthesized and cloned into the pTrimer-T0(M) vector between HindIII and BgiII sites to allow in-frame fusion with the C-prodomain of human type I(α) collagen with a mutated BMP-1 site and some glycine-rich region upstream. A short cDNA sequence encoding human TNFRII signal peptide was subsequently cloned into the HindIII site in front of the mature TRAIL to direct the secretion of the pro-TRAIL-Trimer secretion. The entire vector designated as pGH-313D was transfected into GH-CHO (dhfr–/–) cells and selected for high titer producers by step-wise gene amplification under MTX selections. The secreted mature TRAIL-Trimer with signal peptide cleaved has an amino acid sequence specified as either SEQ ID NO: 1 or SEQ ID NO: 2 and a 3D structure of a disulfide bond-linked Trimer denoted in FIG. 1. In contrast, the native TRAIL, which is a non-covalent linked homo-trimer, is structurally less stable as depicted in FIG. 1. As a control the same strategy was employed to create a TRAIL-Fc fusion expression construct using phFc vector (GenHunter) to allow secretion of mature TRAIL-Fc dimeric fusion protein (FIG. 1).

Figure 2:
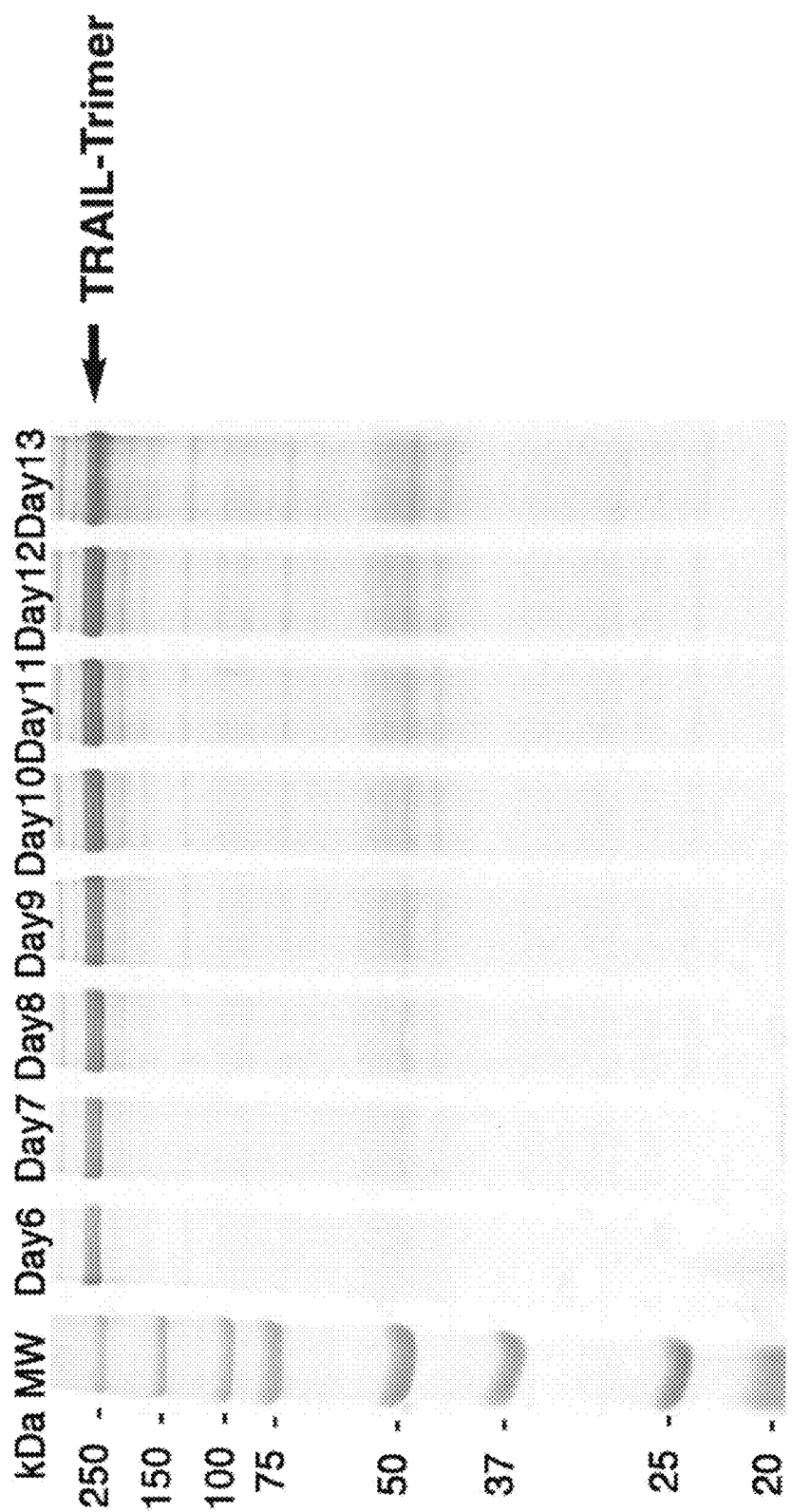
FIG. 2 is SDS-PAGE analysis by Coomasie blue staining of high level expression of TRAIL-Trimer (SEQ ID NO: 1) in GH-CHO cells (GenHunter Corporation) in a serum free fed-batch bioprocess over 13 days in a 10 L bioreactor (NBS). Cells were seed at 0.3 million/mL and cultured in SFM4CHO medium (Hyclone) and 10% Cell Boost 2 (Hyclone) was fed every other day from Day 4. 10 microliter of cell culture media from each day were analyzed under either non-reducing or reducing condition to demonstrate that TRAIL-Trimer was covalently (disulfide bonds) linked homo-trimer as indicated. The molecular weight marker (Tru Blue, from BioRad) was used as control. The estimated final titer of TRAIL-Trimer expression was around 0.4 mg/mL.
Figure 3:
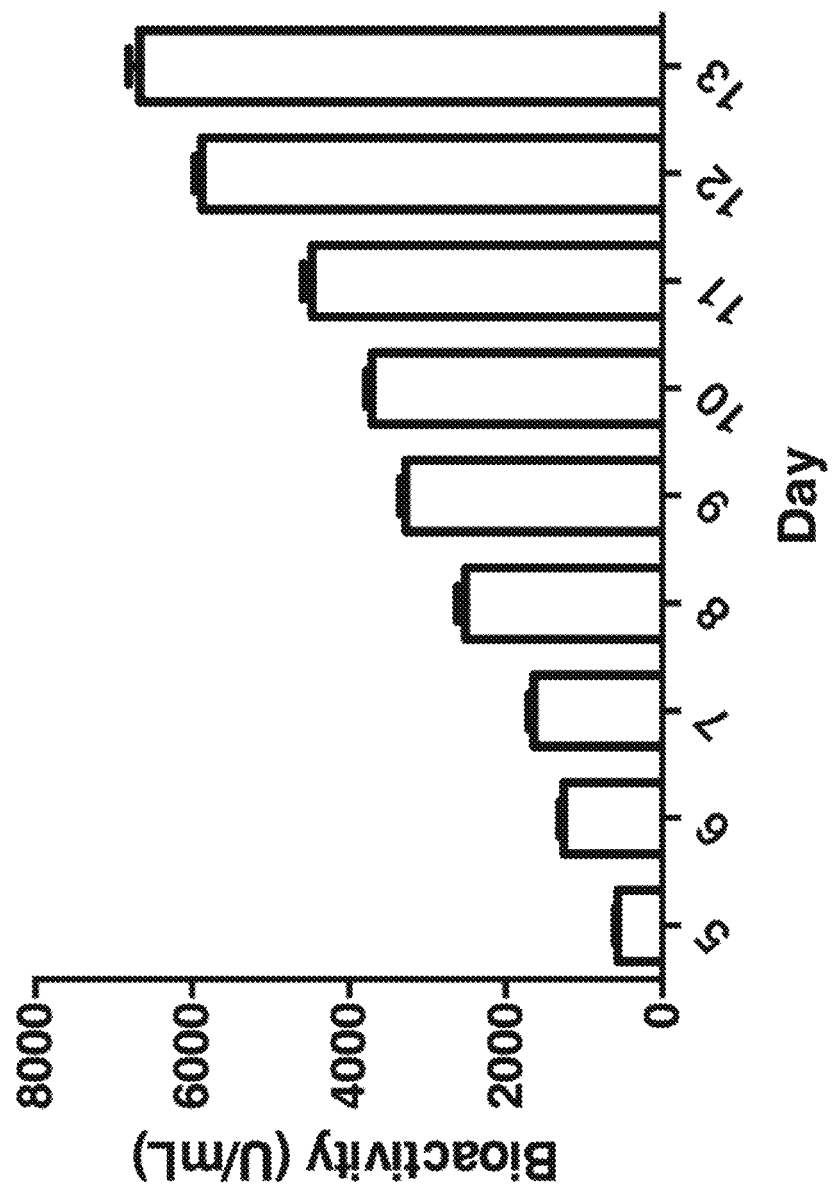
FIG. 3 is bioassay analysis of TRAIL-Trimer production in conditioned medium from Day to Day 13 from the fed-batch cell culture of CHO cells overexpressing TRAIL-Trimer.

To produce highly pure and sufficient amounts of TRAIL-Trimer fusion protein for functional analyses, we began by screening for high-titer production clones of TRAIL-Trimer vector-transfected CHO cells via MTX-mediated gene amplification; the resulting leading clone was then adapted to serum free media and grown under fed-batch cell culture process in a bioreactor, which led to high-level expression of TRAIL-Trimer (FIG. 2). During the course of the cell culture process, samples were taken to assess the bioactivity of TRAIL-Trimer using a TRAIL-sensitive human colon cancer derived cell line—COLO205—by MTT staining (FIG. 3); as expected, bioactivity increased over time as the production of TRAIL-Trimer continued.

Figure 4:
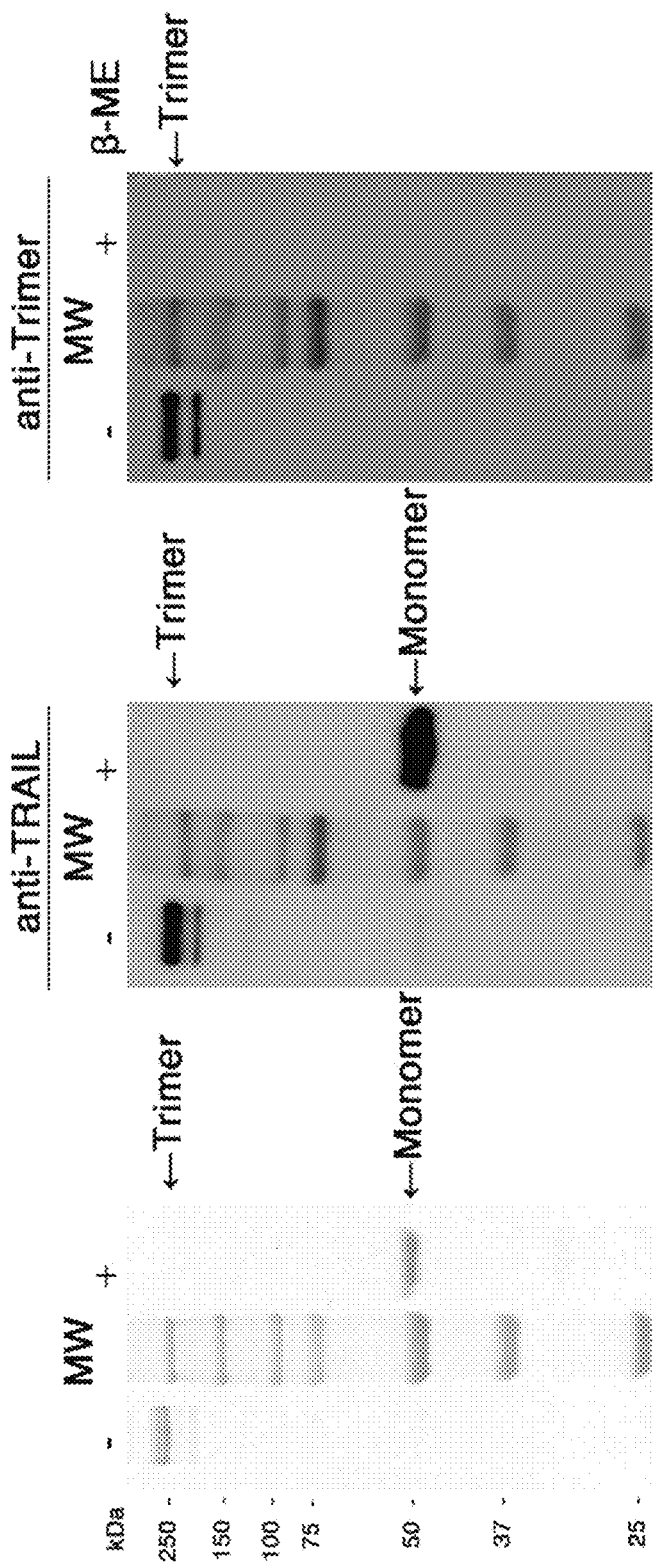
FIG. 4 is SDS-PAGE and Western blot analysis of purified TRAIL-Trimer under either non-reducing or reducing conditions. TRAIL-Trimer was sequentially purified from the cell culture medium with hydrophobic interaction chromatography (HIC) followed by ultrafiltration (UF) to change buffer and then via an anion-exchange chromatography (Q) with a 0.2M NaCl elution in 10 mM Tris-Cl, pH 8.2 buffer. After a final polishing with Seperdex 200 gel filtration chromatography (GE health Sciences), the final purified TRAIL-Trimer was more than 90% pure with an IC50 about 100 ng/mL (1 U). Two µg of purified protein was analyzed by a 10% SDS-PAGE and stained with Coomassie Blue. 0.2 µg of purified protein was analyzed by Western blot using monoclonal antibody against TRAIL-domain and Trimer-domain, respectively.

To obtain the TRAIL-Trimer in a highly pure form, TRAIL-Trimer from serum-free conditioned medium was purified to homogeneity by consecutive chromatographic separation steps using Blue Sepharose, Capto Q cloumn and gel filtration. The purified TRAIL-Trimer fusion protein was characterized by SDS-PAGE under either non-reducing or reducing conditions followed by Coomassie blue staining (FIG. 4, left panel). The results clearly indicated that TRAIL-Trimer formed a disulfide bond-linked trimer as predicted. Western blot analysis using either a polyclonal antibody detecting human native TRAIL or a monoclonal antibody specific to the Trimer-Tag™ domain confirmed the structural feature and integrity of the fusion protein (FIG. 4, middle and right panels), which existed essentially as a covalently-linked homotrimer under non-reducing conditions. It was evident that the monoclonal antibody to the Trimer-Tag™ domain could only recognize the epitope under the non-reducing condition, consistent with the structure of the antigen used for the immunization to generate the antibody.

Structural Comparison of TRAIL-Trimer, TRAIL-Fc and Native TRAIL

Figure 5:
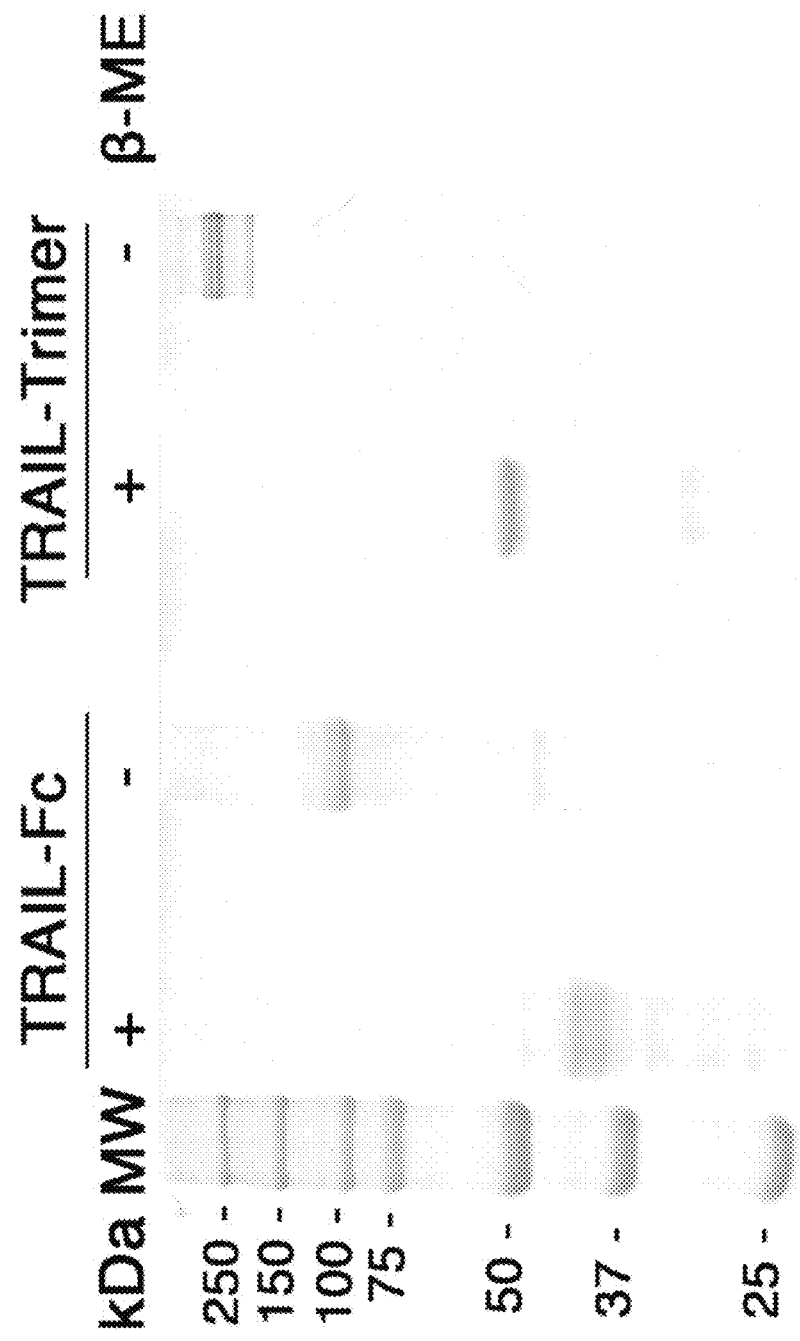
FIG. 5 is purity evaluation of TRAIL-Trimer and TRAIL-Fc. SDS-PAGE analysis of purified TRAIL-Trimer and TRAIL-Fc under either non-reducing or reducing conditions. 2 µg of purified protein was analyzed by 10% or 15% SDS-PAGE, respectively, and stained with Coomassie Blue.

To systematically compare TRAIL-Trimer with either a dimeric TRAIL (dulanermin) or a native TRAIL, we also produced a recombinant TRAIL-Fc fusion protein from CHO cells and native TRAIL from *E. coli*, following the strategy of dulanermin production (FIG. 1). After purification, all three proteins were analyzed first by SDS-PAGE under both non-reducing and reducing conditions to verify their respective structures. The results confirmed that TRAIL-Trimer maintained a homotrimer structure, whereas TRAIL-Fc was a disulfide bond-linked dimer, and native TRAIL was noncovalently-linked trimer (FIG. 5), consistent with previous studies indicating that the homotrimer of native TRAIL is maintained via hydrophobic interfaces on adjacent subunits that are weak and noncovalent in nature.

Comparison of TRAIL-Trimer, TRAIL-Fc and Native TRAIL Bioactivity In Vitro

Figure 6:
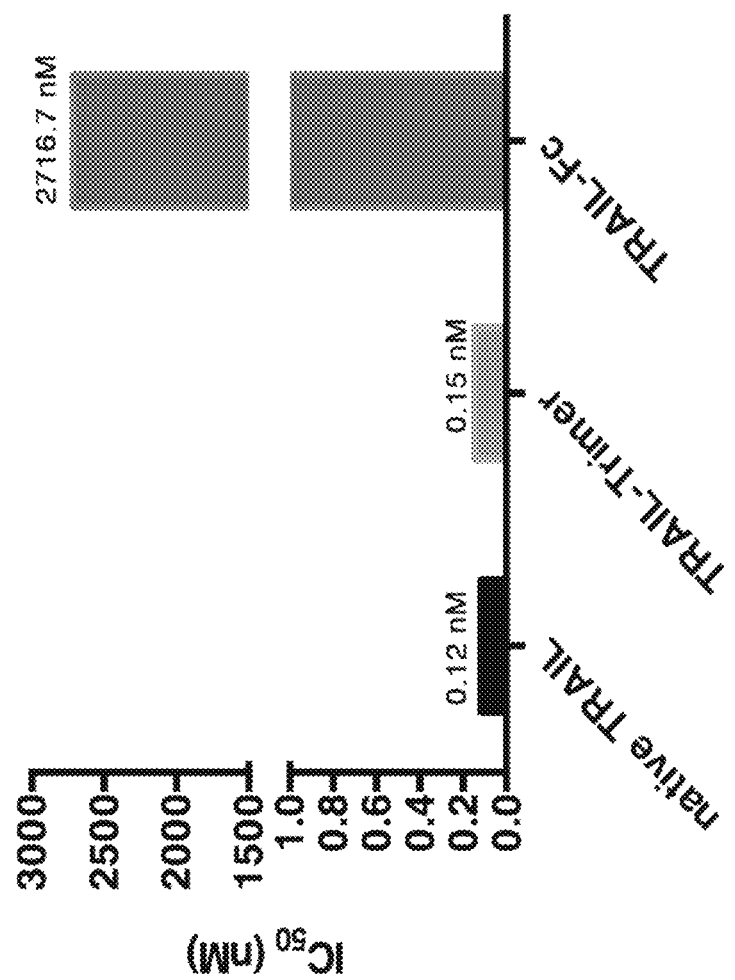
FIG. 6 is the comparison of bioactivity for TRAIL-Trimer, TRAIL-Fc and native TRAIL. The $IC_{50}$ value of TRAIL-Trimer, TRAIL-Fc and native TRAIL were assessed using a TRAIL sensitive cell line COLO205 on a Real-Time Cell Analysis (RTCA) system. The $IC_{50}$ value was obtained according to the dose-response cell index (CI) curve. The IC50 value of TRAIL-Trimer, TRAIL-Fc and native TRAIL is 23.2 ng/mL, 260.8 µg/mL, and 6.7 ng/mL, respectively, before $IC_{50}$ values were molar ratio-adjusted based on theoretical molecular weights for each protein.

The bioactivity $IC_{50}$ values of TRAIL-Trimer, TRAIL-Fc and native TRAIL were assessed using a TRAIL-sensitive human colon cancer cell line—COLO205—via Real-Time Cell Analysis (RTCA) system. Dose-response curves were generated based on cell viability, and the $IC_{50}$ values were obtained according to the dose-response cell index (CI) curve. COLO205 cells were exposed to increasing concentrations of TRAIL-Trimer, TRAIL-Fc or native TRAIL for 16 hr, and $IC_{50}$ values for TRAIL-Trimer, TRAIL-Fc and native TRAIL were determined to be 23.2 ng/ml, 260.8 µg/mL and 6.7 ng/mL, respectively. Because the predicted molecular weights of TRAIL-Trimer (~162 kDa) and TRAIL-Fc (~96 kDa) are both significantly larger than native TRAIL (~60 kDa) due to their fused Trimer-Tag™ and Fc domains respectively (FIG. 1), we then calculated the molar ratio-adjusted $IC_{50}$ values in order to more accurately compare the bioactivities of TRAIL-domains present in each protein. On a molar ratio-adjusted basis, the $IC_{50}$ values for TRAIL-Trimer, TRAIL-Fc and native TRAIL were 0.12 nM, 2716.7 nM and 0.15 nM, respectively (FIG. 6). These results demonstrate that the bioactivity of trimeric forms of TRAIL is over 4 orders of magnitude higher than that of dimeric TRAIL, which may explain why previous agonist mAbs to DR4 and DR5 failed in clinical trials. A previous concern for TRAIL-Trimer was if the natural bioactivity of the trimeric TRAIL conformation could be preserved in the fusion protein; the results presented here clearly demonstrate that the bioactivities of TRAIL-Trimer and native TRAIL are equivalent.

Comparison of TRAIL-Trimer, TRAIL-Fc and Native TRAIL in Receptor Binding

Figure 7:
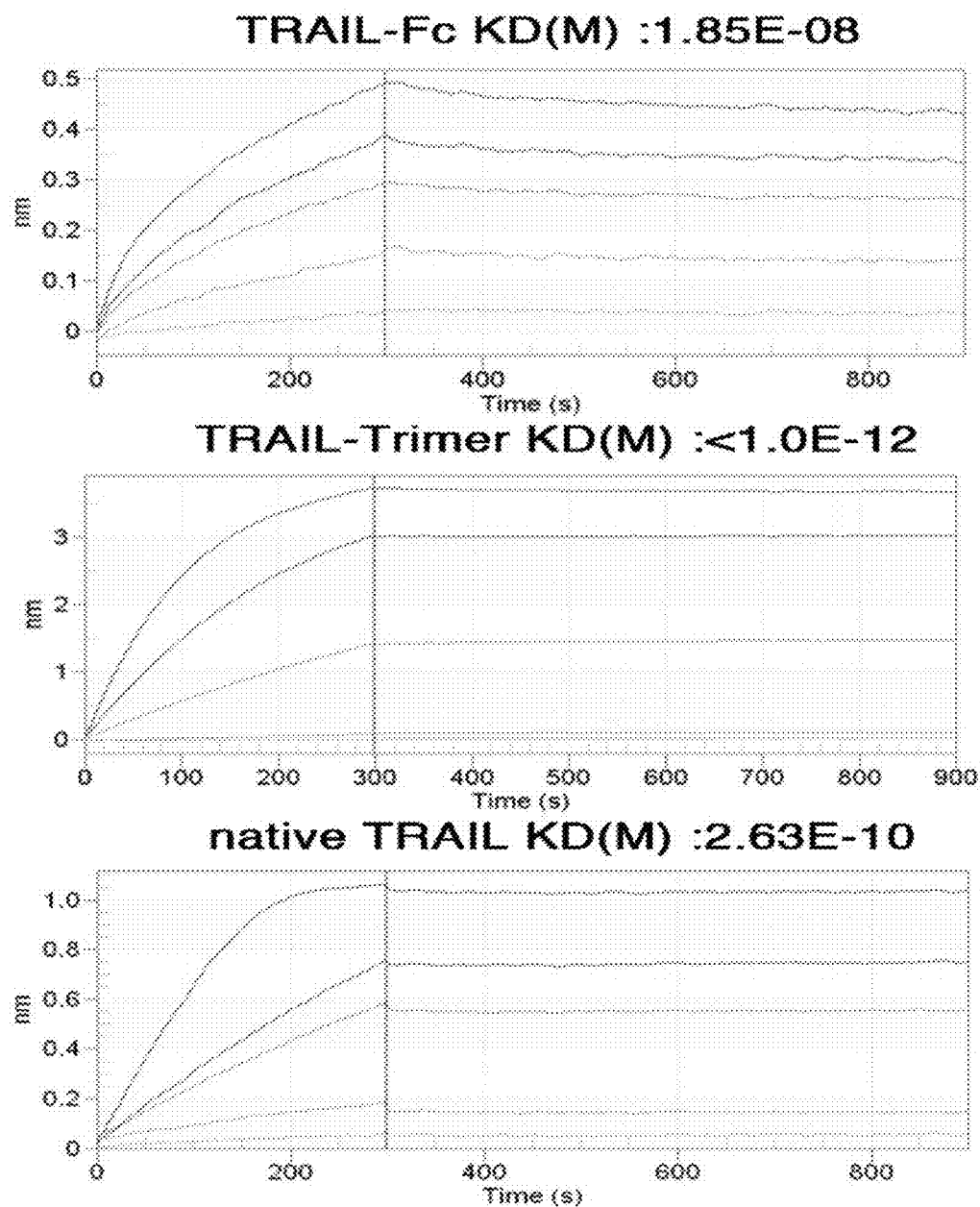
FIG. 7 is the kinetic studies of TRAIL-Trimer, TRAIL-Fc and native TRAIL binding to the soluble DR5-Fc fusion protein assessed by biolayer interferometry measurements. The Super Streptavidin biosensor tips of the ForteBio Octet RED 96 were coated with biotinylated DR5-Fc. The biosensor tips were dipped in increasing concentrations gradient of TRAIL-Trimer, TRAIL-Fc and native TRAIL to measure their binding to DR5-Fc and subsequently moved to wells containing buffer (PBS) to measure dissociation rates. The dissociation constant Kd was shown for each graph.

Avidity In Vitro DR5 (TRAIL-R2) is one of TRAIL's functional receptors which initiates extrinsic apoptosis pathway signaling upon activation; thus, we examined the binding kinetic profile of TRAIL-Trimer, TRAIL-Fc and native TRAIL to a soluble DR5-Fc fusion protein. With Fortebio biolayer interferometry measurement, the biotin-labeled DR5-Fc was first captured on Streptavidin (SA) sensors, and real-time binding curves were measured and plotted by applying the sensor in gradient concentrations (15.4 nM-123.5 nM) of the three analytes (FIG. 7). TRAIL-Trimer was observed to have picomolar binding affinity to DR5-Fc ($K_D$<1.0×10$^{-12}$M). Unsurprisingly, the dimeric TRAIL-Fc exhibited a receptor binding affinity over 4 orders of magnitude lower ($K_D$=1.85×10$^{-8}$M) than that of TRAIL-Trimer. Interestingly, the DR5-Fc binding affinity of TRAIL-Trimer was over two orders of magnitude higher than that of native TRAIL ($K_D$ of 2.63×10$^{-10}$M). While native TRAIL bound to DR5-Fc ($K_{on}$=1.75×10$^5$ Ms$^{-1}$) twice as fast as TRAIL-Trimer ($K_{on}$=8.1×10$^4$ Ms$^{-1}$), native TRAIL dissociated ($K_{off}$=4.6×10$^{-5}$ s$^{-1}$) from DR5-Fc at a rate >460 times faster than TRAIL-Trimer ($K_{off}$<1×10$^{-7}$ s$^{-1}$). This is consistent with the trimeric conformation being the fully active form for TNF family of cytokines and explained why DR4 and DR4 receptor agonist antibodies (made by Human Genome Sciences Inc. and Amgen), which were all dimeric in structures, had low activity and failed in multiple human clinical trials against cancer. This is also why often anti-Fc antibodies are needed to enhance the potency of such agonist antibodies by cross-linking them to oligomers.

These results suggest that the covalent nature of the homotrimeric linkages in TRAIL-Trimer may stabilize the ligand-receptor binding, while the noncovalent trimerization of native TRAIL assumes a conformation more susceptible to dissociation form the receptor.

Pharmacokinetic Profile of TRAIL-Trimer Vs. Native TRAIL in Mice

Figure 8:
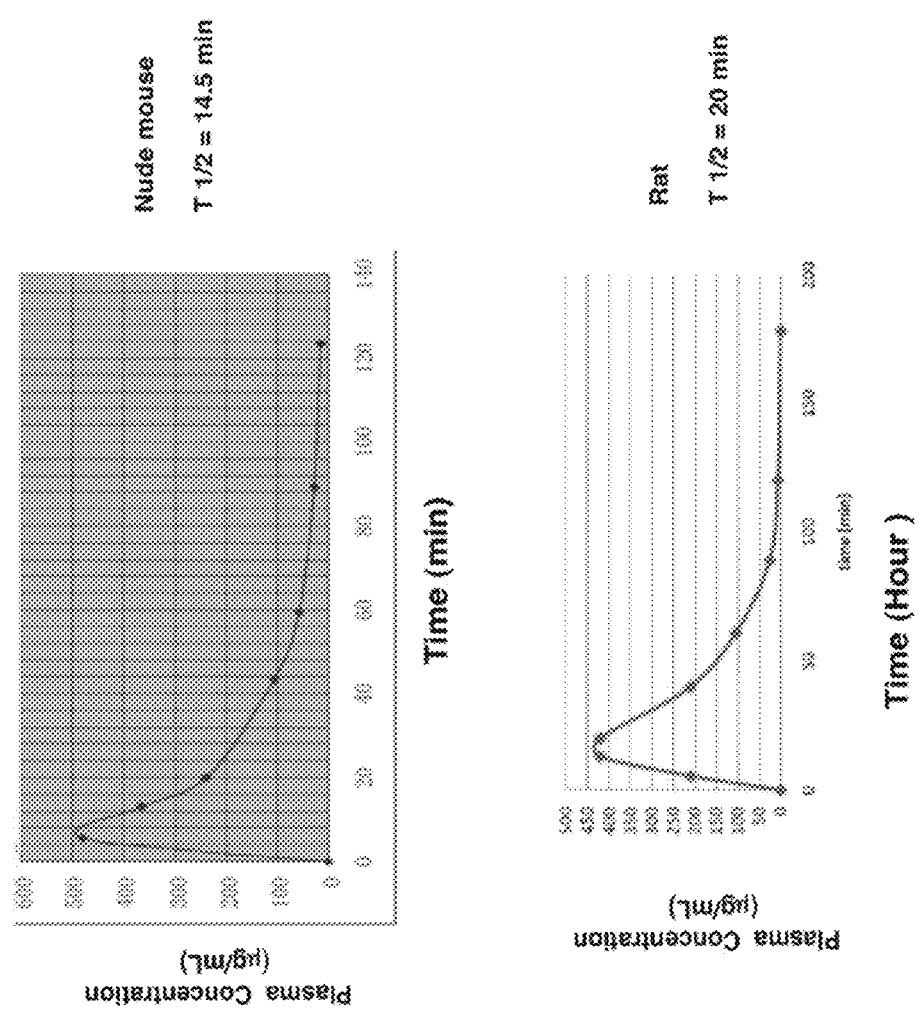
FIG. 8 is PHARMACOKINETIC PROFILE OF TRAIL-TRIMER DETERMINED BY TRAIL BIOASSAY WITH COLO205 CELLS. Mice and rats were injected intravenously with TRAIL-Trimer at 80 mg/kg (n=5 for each species). Relative serum concentrations of TRAIL-Trimer were evaluated at periodic intervals by TRAIL BIOASSAY WITH COLO205 CELLS.

We examined the pharmacokinetic profiles for TRAIL-Trimer; nude mice and Lewis rats were injected intravenously (i.v.) with TRAIL-Trimer (80 mg/kg), and relative serum concentration of the protein was evaluated at periodic intervals by TRAL bioassay using colo 205 cells. The half-life of TRAIL-Trimer was determined to be 24.5 min and 20 min for nude mice and Lewis rats, respectively (FIG. 8), representing an approximately 5-fold longer half-life than that of native TRAIL previously reported. These results indicate that TRAIL-Trimer is less rapidly eliminated and is more stable than native TRAIL in vivo.

Comparison of Antitumor Activity of TRAIL-Trimer and Native TRAIL In Vivo

Figure 9:
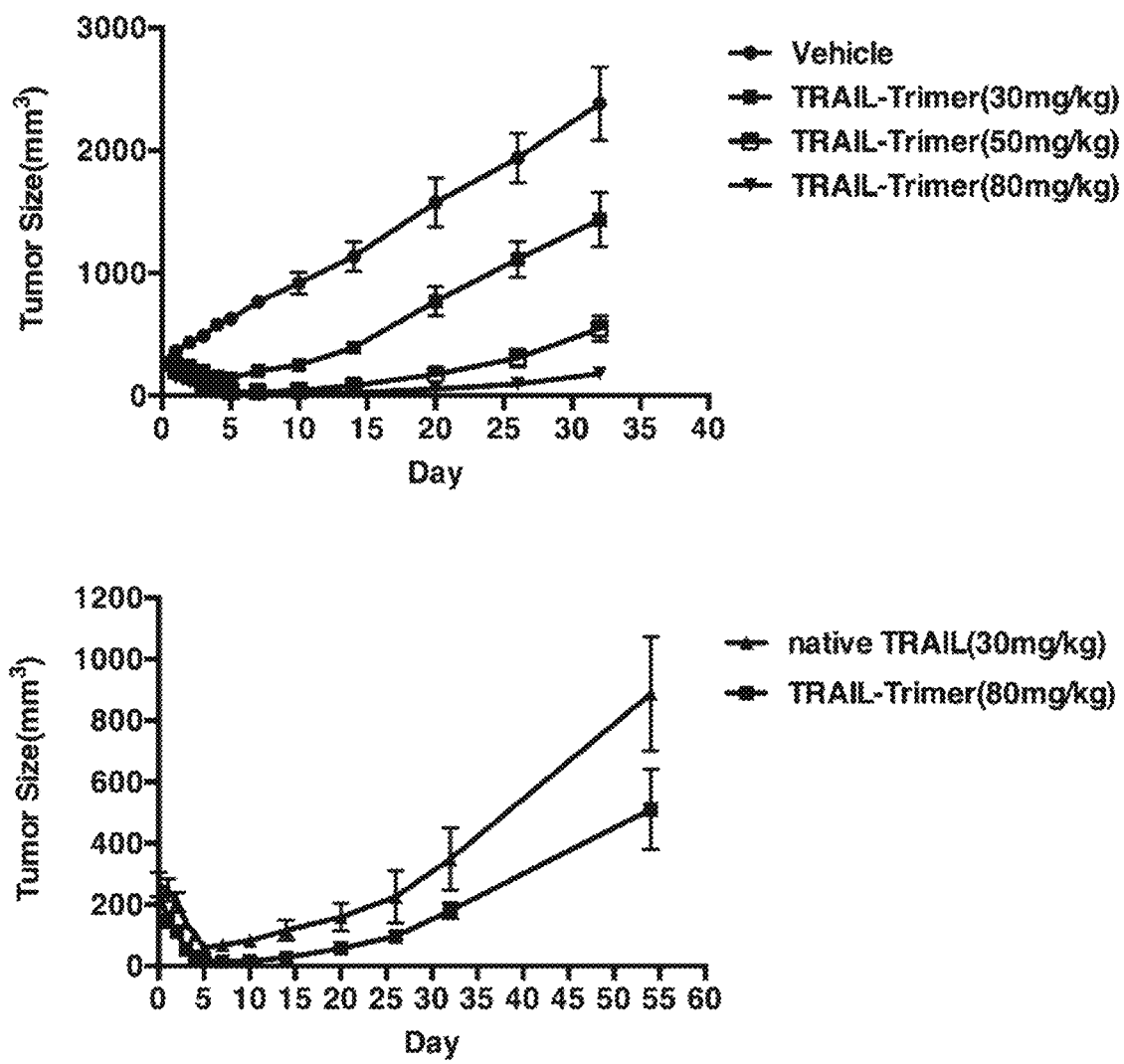
FIG. 9 is the in vivo antitumor activities of TRAIL-Trimer and native TRAIL. (Upper panel) Nude mice with established COLO205 xenografts were given TRAIL-Trimer (30, 50, or 80 mg/kg/day) or vehicle as an i.v. bolus for 5 consecutive days (n=6/group). Results shown are group mean (±S.D.). (Lower panel) Nude mice with established COLO205 xenografts were given the same molar concentration of TRAIL-Trimer (80 mg/kg/day) and native TRAIL (30 mg/kg/day). Results shown are group mean (±S.D.).

We then examined the ability of TRAIL-Trimer and native TRAIL to kill human tumor cells in vivo by using a common tumor xenograft model in nude mice. After subcutaneous tumors from inoculated COLO205 human colon cancer cell line had grown to an average size of ~270 mm$^3$, mice were randomized (n=6/group), and TRAIL-Trimer doses of 30 mg/kg, 50 mg/kg or 80 mg/kg were given intravenously once-daily over the first 5 days of the study. Tumor sizes rapidly decreased following TRAIL-Trimer administration in a dose-dependent fashion (FIG. 9, upper panel). In contrast, tumors from mice that had been administered with formulation buffer (negative control) grew rapidly and continuously.

The dose-response of TRAIL-Trimer observed here suggests that the best antitumor activity with this regimen is achieved with 80 mg/kg/day, where the longest sustained antitumor response was observed. Thus, we then compared the efficacy of TRAIL-Trimer (80 mg/kg/day) to an equimolar dose of native TRAIL (30 mg/kg/day), given the approximately 2.7 fold difference in molecular weight between the two proteins. At every time point that tumor sizes were measured following dosing, tumors in mice treated with TRAIL-Trimer were smaller than in mice treated with native TRAIL (FIG. 9, lower panel), demonstrating that TRAIL-Trimer antitumor activity in vivo is superior to native TRAIL in this model. These results are consistent with the superior systemic exposure (pharmacokinetic profile) and receptor-binding affinity results also observed.

Example 2: Expression, Purification and Functional Characterization of 4-1BBL-Trimer Immunotherapy is a rapidly expanding field in oncology, which mobilizes one's own immune system to combat the cancerous lesions. Although immune-checkpoint inhibitors such as anti-PD-1 and anti-PD-L1 antibodies have generated much excitement in "curing" certain type of deadly cancer, the relatively low response rates in the range of 15-30% indicate a need for further improvement. Of the many approaches currently under studying to boost anti-tumor immune responses, modulation of immune co-stimulatory receptors on lymphocytes in the tumor microenvironment has thus far proven to be the most promising. Lymphocytes require two signals for optimal activation T-cell receptor (TCR) ligation and costimulation. Costimulation provides an independent stimulus that influences the outcome of the interaction between T cells and antigen-presenting cells (APC). Without costimulation antigen primed T cells will undergo apoptosis or become anergic. 4-1BB (CD137) and OX40 are costimulatory members of the TNFR family, which are induced when T cells receive antigen-specific signals. Their ligands, 4-1BBL (CD137L) and OX40L, are also induced on antigen-presenting cells, such as dendritic cells, macrophages, and B cells. The 4-1BBL-4-1BB pathway co-stimulates T cells to carry out effector functions such as eradication of established tumors and the broadening of primary and memory CD8 T cell responses. 4-1BB-mediated signals have been shown to induce a novel subpopulation of $CD11c^+CD8^+T$ cells that have strong anti-cancer and anti-autoimmune effects. Binding of the 4-1BB ligand (4-1BBL) to its receptor, 4-1BB provides the T lymphocyte with co-stimulatory signals for survival, proliferation, and differentiation. The 4-1BBL pathway is becoming a well-known target for anti-cancer immunotherapy. In contrast to immune checkpoint blocking antibodies, 4-1BB agonists can both potentiate anti-tumor and anti-viral immunity, while at the same time ameliorating autoimmune diseases.

Figure 10A:
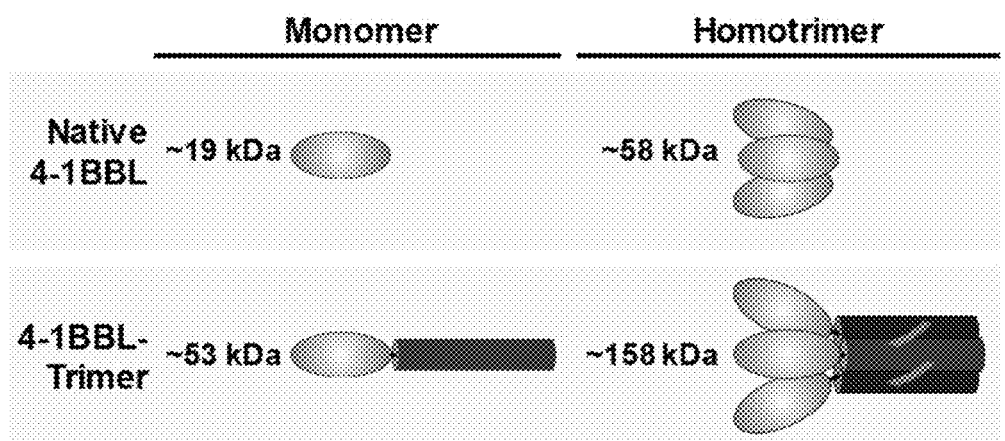
FIG. 10A is a schematic representation of structural differences of 4-1BBL polypeptides used in this study. Upper panel: Two recombinant soluble forms of human 4-1BBL has been used in this study: a native 4-1BBL comprised of the extracellular domain of 4-1BBL, and a 4-1BBL-Trimer comprised of extracellular 4-1BBL domain fused to the C-prodomain of a Type I collagen (Trimer-Tag™) with a mutated BMP-1 site. Theoretical molecular weights (kDa) of both monomeric and multimeric forms of native 4-1BBL and 4-1BBL-Trimer were as indicated, respectively. Native 4-1BBL associates into a noncovalently-linked homotrimer, whereas 4-1BBL-Trimer forms a covalently-linked homotrimer.
Figure 10B:
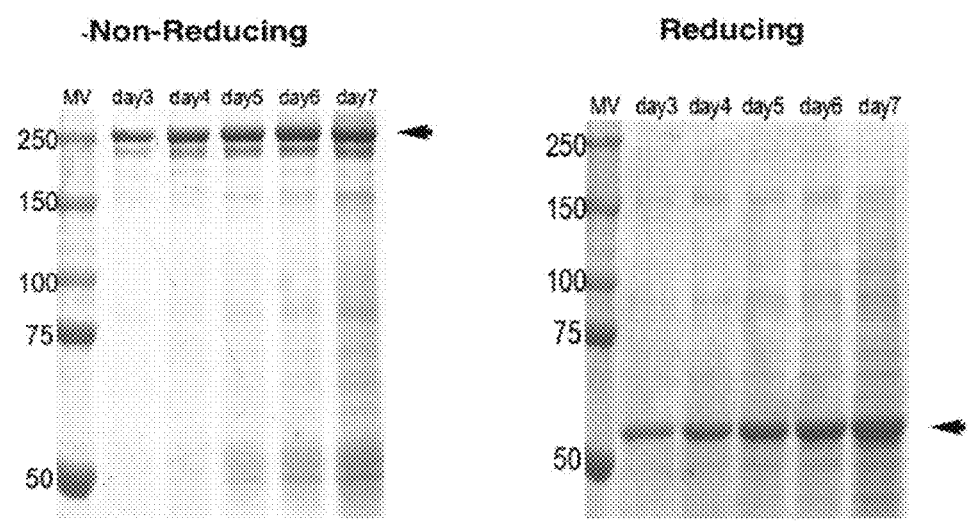
FIG. 10B is SDS-PAGE analysis by Coomasie blue staining of high level expression of human 4-1BBL-Trimer (SEQ ID NO: 4) in GH-CHO cells (GenHunter Corporation) in a serum free fed-batch bioprocess over 7 days in a 10 L bioreactor. Cells were seed at 0.3 million/mL and cultured in SFM4CHO medium (Hyclone) and 10% Cell Boost 2 (Hyclone) was fed every other day from Day 4. 10 microliter of cell culture media from each day were analyzed under either non-reducing (Left Panel) or reducing condition (right panel) to demonstrate that 4-1BBL-Trimer was covalently (disulfide bonds) linked homo-trimer as indicated by arrow heads. The molecular weight marker (Tru Blue, from Bio-Rad) was used as control.
Figure 11:
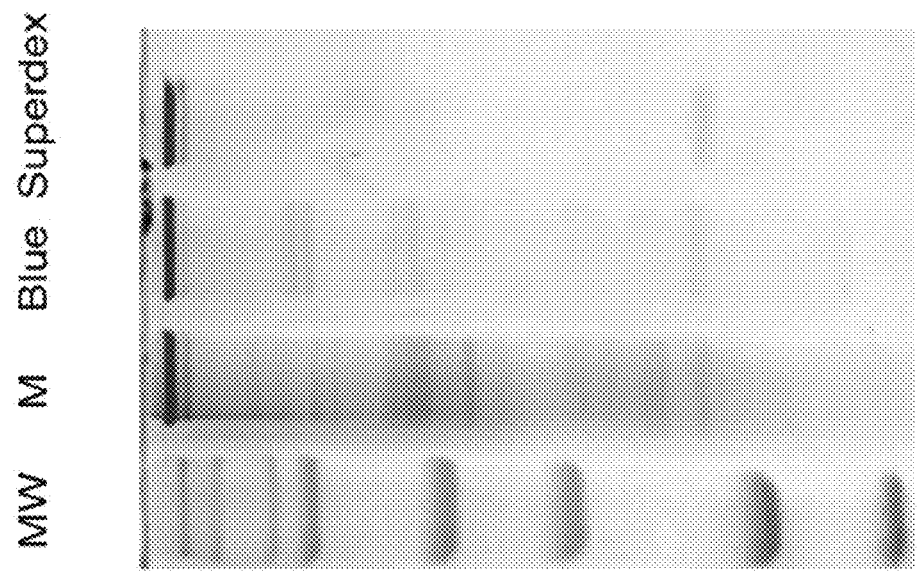
FIG. 11 is SDS-PAGE analysis of purified 4-1BBL-Trimer under non-reducing condition. 4-1BBL-Trimer was expressed in CHO cells under serum-free condition and sequentially purified from the cell culture medium (M) with Blue Sepharose chromatography (Blue) followed by ultrafiltration (UF) to change buffer and concentration, and then via Superdex 200 gel filtration chromatography. The molecular weight size markers (MW) were as in FIG. 2.
Figure 12:
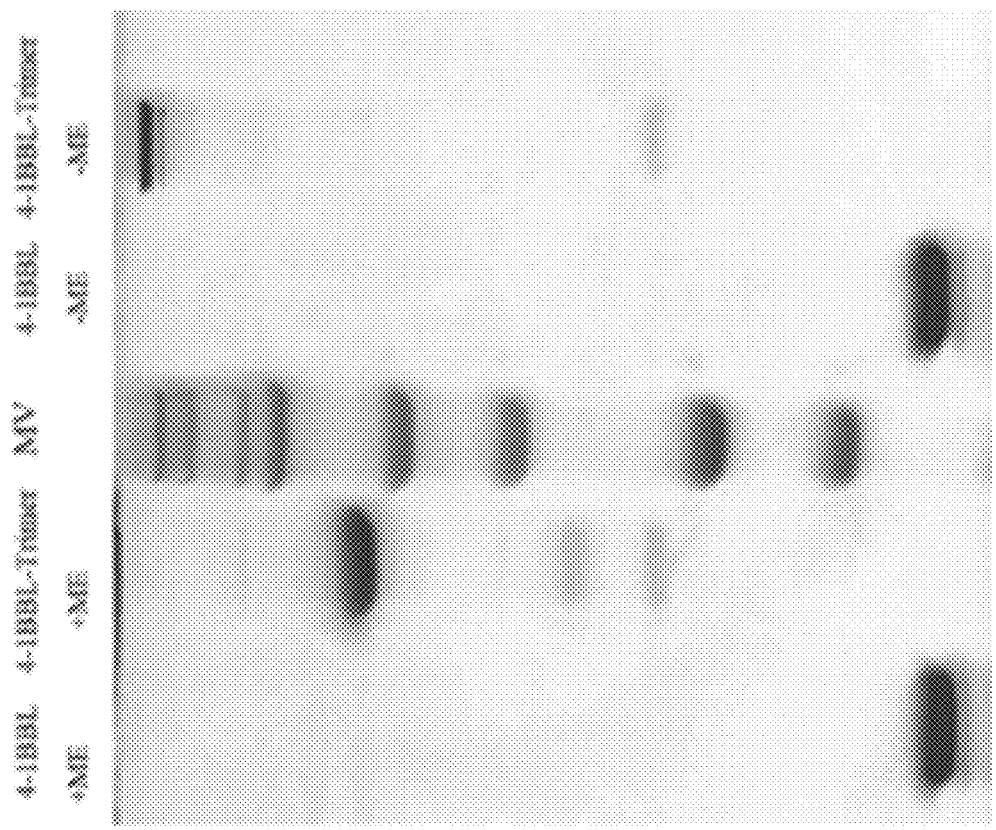
FIG. 12 is SDS-PAGE analysis of purified 4-1BBL and 4-1BBL-Trimer under either non-reducing or reducing conditions. Note the purified native-like 4-1BBL expressed in *E. coli*, unlike 4-1BBL-Trimer is a disulfide bond linked trimer. The molecular weight size markers (MW) were as in FIG. 2.
Figure 13A:
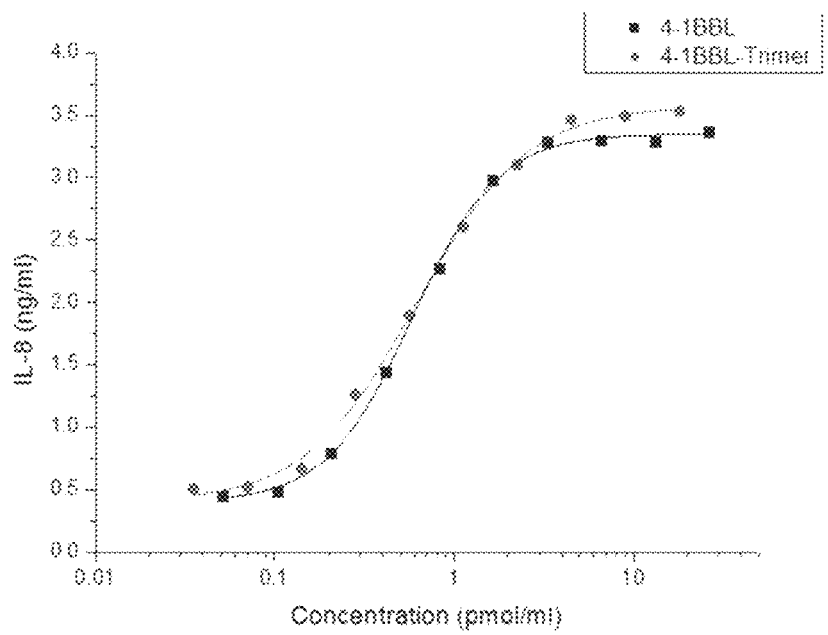
FIG. 13A is functional characterization of purified 4-1BBL vs. 4-1BBL-Trimer in stimulation of PBMC production of IL-8. Both 4-1BBL vs. 4-1BBL-Trimer had similar IC50 in stimulating PBMC in IL-8 production, with IC50 being 0.5-0.6 pmole/mL.
Figure 13B:
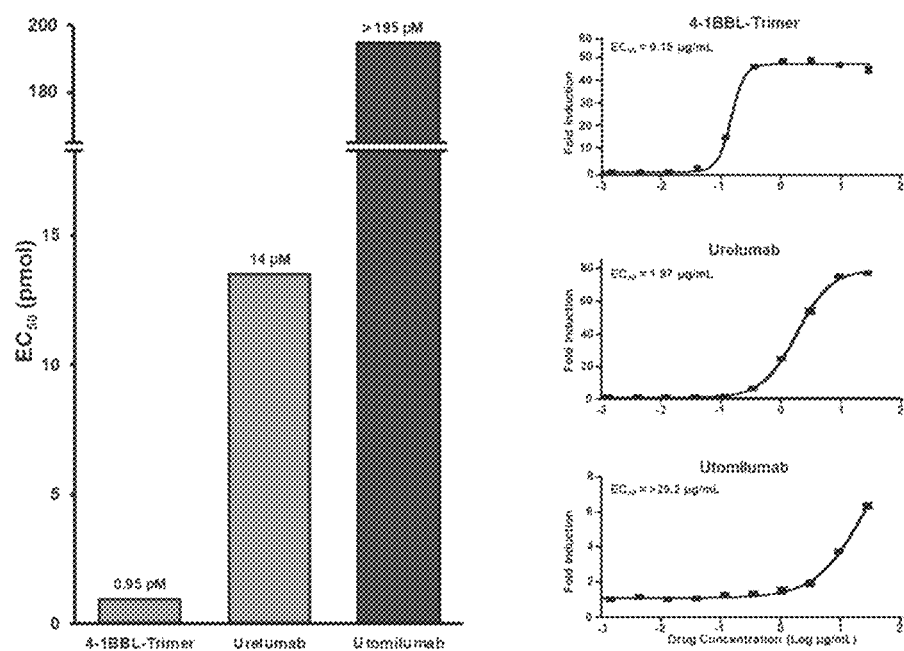
FIG. 13B is bioactivity comparison of 4-1BBL-Trimer, native 4-1BBL and 4-1BB agonist mAbs. Bioactivities of various 4-1BB agonists were evaluated in a 4-1BB/NFkB reporter—HEK293 cell-based assay, and $EC_{50}$ values were obtained according to the dose-response curves (the lower the EC50, the higher the affinity thus more potent in 4-1BB receptor activation). 4-1BBL-Trimer was 1-2 orders of magnitude more potent than the 4-1BB agonist mAbs.

In this invention, we also used Trimer-Tag™ technology developed in our laboratory to a create disulfide-bond linked 4-1BBL-Trimer (FIG. 10A) and expressed the recombinant fusion protein in CHO cells (FIG. 10B), following the same strategy as described above for TRAIL-Trimer. The secreted mature 4-1BBL-Trimer with signal peptide cleaved has an amino acid sequence specified as either SEQ ID NO: 3 or SEQ ID NO: 4. 4-1BBL-Trimer was purified to near homogeneity using multiple chromatography approaches including Blue-Sepharose and Superdex 200 gel filtration chromatography (FIG. 11) and shown to be a disulfide bond-linked trimer in comparison to recombinant native-like 4-1BBL which is not a covalently linked trimer (FIG. 12). We show that the purified 4-1BBL-Trimer has similar biological activity as native 4-1BBL in activating PBMC, which leads to IL-8 production (FIG. 13A). A side-by-side functional test was also carried out to compare 4-1BBL-Trimer with agonistic 4-1BB monoclonal antibodies in a 4-1BB/NFkB reporter—HEK293 cell-based functional assay. 4-1BBL-Trimer showed over 1-2 order higher biological activity (lower EC50) in receptor activation than both 4-1BB monoclonal antibodies (FIG. 13B). Thus the recombinant 4-1BBL and 4-1BBL-Trimer may be used as more potential immuno-costimulators in the next generation of immune-oncology drugs than 4-1BB agonist monoclonal antibodies (mAbs). These 4-1BB agonist mAbs were also reported to have either exhibited extensive liver toxicity or little efficacy in cancer patients, consistent with their long half-lives and poor activity.

We also demonstrated that 4-1BBL-Trimer has potent antitumor activity in vivo driven by immune activation. Given that 4-1BBL-Trimer is a human fusion protein, humanized C57BL/6 mice homozygous for hCD137 (4-1BB, receptor for 4-1BBL) knock-in and with established subcutaneous mc38 colon cancer tumor xenografts were utilized for 4-1BBL-Trimer antitumor efficacy experiments. In a dose-ranging study, we demonstrated that 4-1BBL-Trimer administered at doses at or above 5 mg/kg were effective in inhibiting tumor growth (FIG. 14A, left). We further demonstrated that 4-1BBL-Trimer administered in a single induction regimen (Days 0, 1, 2) achieved similar efficacy to continuous dosing (FIG. 14B, right), suggesting that an induction dosing scheme may be critical for stimulating cytotoxic antitumor immune response, and additional maintenance dosing schemes should be further evaluated. Mice from these experiments were sacrificed at Day 21, and tumors were harvested for tumor-infiltrating lymphocyte (TIL) evaluation via FACS (FIG. 14B), confirming that 4-1BBL-Trimer antitumor activity was correlated with an increase in CD4+, CD8+ and NK TILs, consistent with more potent immune activation. 4-1BBL-Trimer in vivo antitumor activity was further evaluated for potential antitumor synergies with a PD-1 monoclonal antibody (FIG. 15). Mice with double knock-in for hCD137 and hPD-1 genes administered with both 4-1BBL-Trimer and PD-1 monoclonal antibody KEYTRUDA® (pembrolizumab) from Merck achieved significantly greater mc38 tumor growth inhibition than either 4-1BBL-Trimer or PD-1 mAb alone. These results suggest that immune activation by 4-1BBL-Trimer (like pressing a gas paddle in a car) and anti-PD-1 antibody (like loosening the brake) could have a synergistic effect in tumor regression.

Example 3: Expression, Purification and Functional Characterization of OX40L-Trimer Since OX40L has similar biological functions as 4-1BBL, we also produced OX40L-Trimer following the same strategy. The secreted mature OX40L-Trimer with signal peptide cleaved has an amino acid sequence specified as either SEQ ID NO: 5 or SEQ ID NO: 6.

Example 4: Pharmacokinetic Profiles of TRAIL-Trimer and Native Trail in Tumor Ascites and In Vivo Anti-Tumor Activity TRAIL-Trimer Against Human Cancer Cells Derived from Metastatic Ascites of Human Gastric Cancer Balb/c mice with ascites developed via inoculation of a hybridoma cell line were injected intraperitoneally with either 10 mg/kg (upper panel) or 80 mg/kg (lower panel) of TRAIL-Trimer (n=2 for each dosing). Relative concentration of TRAIL-Trimer was evaluated at periodic intervals using the standard bioassay (colo205 cells) and fluid taken from the ascites. Rather surprisingly, the half-life of TRAIL-Trimer was shown to be in the range of 4-5 hrs (FIG. 16). Interestingly, we showed that the native TRAIL (10 mg/kg) also was turned over much slower in tumor ascites than that in sera, with a half-life around 2 hrs (FIG. 17), in comparison to 3-5 min in sera via i.v. injection. Compared to their quick elimination in sera, the extremely long half-lives of both TRAIL-Trimer and native TRAIL discovered in our studies immediately suggest that treatment of metastatic ascites caused by the tumor cells metastasized to the stomach cavity may be an ideal indication for both TRAIL-Trimer and native TRAIL.

To this end, we went on to demonstrate the efficacy in vivo antitumor activities of TRAIL-Trimer against SNU-16 which is a human gastric cancer cell line established from metastatic ascites. Nude mice with established subcutaneous xenografts of SNU-16 cells were given TRAIL-Trimer (20, 40, or 80 mg/kg/day) or vehicle as an i.v. bolus for 5 consecutive days (n=6/group). As a control, we also delivered TRAIL-Trimer at 80 mg/kg/day for 5 consecutive days via intraperitoneal injections (n=6/group). The results shown in FIG. 18 demonstrated that, like colo205 cells, human gastric cancer cells derived from metastatic ascites were very sensitive to TRAIL-Trimer via i.v. delivery of the drug. When equal dosage of TRAIL-Trimer (80 mg/kg/day) was administered via intraperitoneal injections (i.p.), the anti-tumor potency was much less compared to that via i.v. delivery of the drug. In fact the anti-tumor activity of TRAIL-Trimer at 80 mg/kg/day via i.p. injection was even less potent than i.v. delivery of the drug at 20 mg/kg/day. This finding confirms that serum absorption of TRAIL-Trimer when delivered via i.p. injection was very slow (<25%), which is consistent with the slow turnover of TRAIL-Trimer in intraperitoneal cavity or ascites fluid as described above.

Example 5: Pharmacodynamic Studies of TRAIL-Trimer Against Human Cancer Cells Derived from Metastatic Pleural Effusion (MPE) of Human Cancer Metastatic pleural effusion (MPE) is the abnormal accumulation of fluid in the pleural cavity in cancer patients, indicating intrapleural dissemination of cancer cells and is typically a grave prognostic sign. Like in metastatic ascites accumulating in the stomach cavity, MPE is caused by growth of cancer cells behind the chest walls and in the lungs where they block the normal drainage of the lymphoid system. Almost all MPE is associated with loss of albumin and dyspnea (shortness of breath) due to the obstruction of lung expansion. Worldwide chemical pleurodesis, utilizing sclerosing agents such as talc, is often performed to manage MPE, but often results in chest pain and has a high failure rate. Pleural aspiration and/or insertion of an indwelling pleural catheter (IPC) for ambulatory MPE drainage are alternative treatment modalities. None of these methods treat the underlying tumor cells, and all have potential risks and recognized complications. Currently, there are no targeted or biologic antitumor therapies approved to reduce production or prevent re-accumulation of MPE. Most often occurring in patients with lung cancer or other malignancies metastatic to the lungs (such as pancreatic cancer, breast cancer, gastrointestinal cancers, lymphoma/hematological malignancies, etc.). MPE remains a major unmet medical need worldwide. Having demonstrated that majority of cancer cell lines derived from metastatic ascites were sensitive to TRAIL-Trimer, we also evaluated multiple cancer cell lines derived from MPE. As expected, cancer cell lines derived from MPE of gastrointestinal cancers and pancreatic cancer, were super-sensitive to TRAIL-Trimer (FIG. 19). These finding support that TRAIL-Trimer may be used to treat MPE, whereby it may kill the cancer cells that block the lymphoid drain and inside the MPE, as well as in the lungs. It is predicted that this would benefit quality of life of the patients and improve survival by stopping continued MPE accumulation, loss of proteins and electrolytes. Like in metastatic ascites which is also believed to be caused by blockage of lymphoid drains in the stomach cavity by cancer cells, we predict that TRAIL-Trimer when given via intrapleural infusion through a two-way catheter pre-installed for fluid drainage will have a much longer half-life in MPE where the drug can more efficiently kill cancer cells, in comparison to systemic drug delivery which results rapid drug clearance through renal filtration as we discussed above.

Previously, immune checkpoint inhibitors such as anti-PD1 and anti-PD-L1 have been reported to work better in controlling tumors sometimes when tumor antigens may be released by chemotherapies first. Thus, we would predict that TRAIL-Trimer which induces cancer cell-specific apoptosis (tumor antigen release), without the toxic side effects of chemotherapies on both normal (inhibition of immune cells) and cancer cells, can be better used in combination with immune checkpoint inhibitors to more efficiently contain the tumor in a long lasting basis. The same concept has been demonstrated for 4-1BBL-Trimer in EXAMPLE 2 above, and 4-1BBL and TRAIL are related in structure and both belong to TNF family of cytokines.

---

What is claimed is:

1. A method for treating cancer in a mammal, comprising a step of administering to said mammal a therapeutically effective amount of a disulfide bond-linked trimeric 4-1BBL fusion protein, wherein the disulfide bond-linked trimeric 4-1BBL the fusion protein comprises the amino acid sequence set forth in SEQ ID NO: 3 or SEQ ID NO: 4.

2. The method of claim 1, wherein the administering step further comprises administration of a therapeutically effective amount of an anti-PD1 antibody along with the therapeutically effective amount of the disulfide bond-linked trimeric 4-1BBL fusion protein.

3. The method of claim 1, wherein the administering step further comprises administration of a therapeutically effective amount of an anti-PD-L1 antibody along with the therapeutically effective amount of the disulfide bond-linked trimeric 4-1BBL fusion protein.

4. The method of claim 1, wherein the cancer is gastrointestinal cancer.

5. The method of claim 1, wherein the cancer is colorectal cancer.

6. The method of claim 1, wherein the cancer is lung cancer.

7. The method of claim 1, wherein the cancer is pancreatic cancer.

8. The method of claim 1, wherein the cancer is ovarian cancer.

9. The method of claim 1, wherein the cancer is a malignant ascites.

10. The method of claim 1, wherein the cancer is peritoneal carcinomatosis.

11. The method of claim 1, wherein the disulfide bond-linked trimeric fusion protein is administered via intravenous injection.

12. The method of claim 1, wherein the disulfide bond-linked trimeric fusion protein is administered via intraperitoneal infusion.

13. The method of claim 1, wherein the disulfide bond-linked trimeric fusion protein is administered via intrapleural infusion.

14. The method of claim 1, wherein the disulfide bond-linked trimeric fusion protein is administered via subcutaneous injection.

15. The method of claim 1, wherein the disulfide bond-linked trimeric fusion protein is administered in a series of doses separated by intervals of days or weeks.

16. The method of claim 1, wherein the disulfide bond-linked trimeric fusion protein is administered in combination with chemotherapy.

17. The method of claim 1, wherein the disulfide bond-linked trimeric fusion protein is administered in combination with a Ras inhibitor.

* * * * *

SEQUENCE LISTING

```
<160> NUMBER OF SEQ ID NOS: 7

<210> SEQ ID NO 1
<211> LENGTH: 479
<212> TYPE: PRT
<213> ORGANISM: Artificial Sequence
<220> FEATURE:
<223> OTHER INFORMATION: FUSION PROTEIN

<400> SEQUENCE: 1

Val Arg Glu Arg Gly Pro Gln Arg Val Ala Ala His Ile Thr Gly Thr
1               5                   10                  15
```

-continued

```
Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
50                  55                  60

Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
130                 135                 140

Val Ser Val Thr Asn Glu His Leu Ile Asp Met Asp His Glu Ala Ser
145                 150                 155                 160

Phe Phe Gly Ala Phe Leu Val Gly Gly Ser Asn Gly Leu Pro Gly Pro
                165                 170                 175

Ile Gly Pro Pro Gly Pro Arg Gly Arg Thr Gly Asp Ala Gly Pro Val
            180                 185                 190

Gly Pro Pro Gly Pro Pro Gly Pro Pro Gly Pro Pro Gly Pro Pro Ser
        195                 200                 205

Ala Gly Phe Asp Phe Ser Phe Leu Pro Gln Pro Pro Gln Glu Lys Ala
210                 215                 220

His Asp Gly Gly Arg Tyr Tyr Arg Ala Asn Asp Ala Asn Val Val Arg
225                 230                 235                 240

Asp Arg Asp Leu Glu Val Asp Thr Thr Leu Lys Ser Leu Ser Gln Gln
                245                 250                 255

Ile Glu Asn Ile Arg Ser Pro Glu Gly Ser Arg Lys Asn Pro Ala Arg
            260                 265                 270

Thr Cys Arg Asp Leu Lys Met Cys His Ser Asp Trp Lys Ser Gly Glu
        275                 280                 285

Tyr Trp Ile Asp Pro Asn Gln Gly Cys Asn Leu Asp Ala Ile Lys Val
290                 295                 300

Phe Cys Asn Met Glu Thr Gly Glu Thr Cys Val Tyr Pro Thr Gln Pro
305                 310                 315                 320

Ser Val Ala Gln Lys Asn Trp Tyr Ile Ser Lys Asn Pro Lys Asp Lys
                325                 330                 335

Arg His Val Trp Phe Gly Glu Ser Met Thr Asp Gly Phe Gln Phe Glu
            340                 345                 350

Tyr Gly Gly Gln Gly Ser Asp Pro Ala Asp Val Ala Ile Gln Leu Thr
        355                 360                 365

Phe Leu Arg Leu Met Ser Thr Glu Ala Ser Gln Asn Ile Thr Tyr His
370                 375                 380

Cys Lys Asn Ser Val Ala Tyr Met Asp Gln Gln Thr Gly Asn Leu Lys
385                 390                 395                 400

Lys Ala Leu Leu Leu Lys Gly Ser Asn Glu Ile Glu Ile Arg Ala Glu
                405                 410                 415

Gly Asn Ser Arg Phe Thr Tyr Ser Val Thr Val Asp Gly Cys Thr Ser
            420                 425                 430
```

His Thr Gly Ala Trp Gly Lys Thr Val Ile Glu Tyr Lys Thr Thr Lys
            435                 440                 445

Ser Ser Arg Leu Pro Ile Ile Asp Val Ala Pro Leu Asp Val Gly Ala
450                 455                 460

Pro Asp Gln Glu Phe Gly Phe Asp Val Gly Pro Val Cys Phe Leu
465                 470                 475

<210> SEQ ID NO 2
<211> LENGTH: 482
<212> TYPE: PRT
<213> ORGANISM: Artificial
<220> FEATURE:
<223> OTHER INFORMATION: Fusion Protein

<400> SEQUENCE: 2

Leu Lys Leu Val Arg Glu Arg Gly Pro Gln Arg Val Ala Ala His Ile
1               5                   10                  15

Thr Gly Thr Arg Gly Arg Ser Asn Thr Leu Ser Ser Pro Asn Ser Lys
                20                  25                  30

Asn Glu Lys Ala Leu Gly Arg Lys Ile Asn Ser Trp Glu Ser Ser Arg
            35                  40                  45

Ser Gly His Ser Phe Leu Ser Asn Leu His Leu Arg Asn Gly Glu Leu
    50                  55                  60

Val Ile His Glu Lys Gly Phe Tyr Tyr Ile Tyr Ser Gln Thr Tyr Phe
65                  70                  75                  80

Arg Phe Gln Glu Glu Ile Lys Glu Asn Thr Lys Asn Asp Lys Gln Met
                85                  90                  95

Val Gln Tyr Ile Tyr Lys Tyr Thr Ser Tyr Pro Asp Pro Ile Leu Leu
            100                 105                 110

Met Lys Ser Ala Arg Asn Ser Cys Trp Ser Lys Asp Ala Glu Tyr Gly
        115                 120                 125

Leu Tyr Ser Ile Tyr Gln Gly Gly Ile Phe Glu Leu Lys Glu Asn Asp
    130                 135                 140

Arg Ile Phe Val Ser Val Thr Asn Glu His Leu Ile Asp Met Asp His
145                 150                 155                 160

Glu Ala Ser Phe Phe Gly Ala Phe Leu Val Gly Gly Ser Asn Gly Leu
                165                 170                 175

Pro Gly Pro Ile Gly Pro Pro Gly Pro Arg Gly Arg Thr Gly Asp Ala
            180                 185                 190

Gly Pro Val Gly Pro Pro Gly Pro Pro Gly Pro Pro Gly Pro Pro Gly
        195                 200                 205

Pro Pro Ser Ala Gly Phe Asp Phe Ser Phe Leu Pro Gln Pro Pro Gln
    210                 215                 220

Glu Lys Ala His Asp Gly Gly Arg Tyr Tyr Arg Ala Asn Asp Ala Asn
225                 230                 235                 240

Val Val Arg Asp Arg Asp Leu Glu Val Asp Thr Thr Leu Lys Ser Leu
                245                 250                 255

Ser Gln Gln Ile Glu Asn Ile Arg Ser Pro Glu Gly Ser Arg Lys Asn
            260                 265                 270

Pro Ala Arg Thr Cys Arg Asp Leu Lys Met Cys His Ser Asp Trp Lys
        275                 280                 285

Ser Gly Glu Tyr Trp Ile Asp Pro Asn Gln Gly Cys Asn Leu Asp Ala
    290                 295                 300

Ile Lys Val Phe Cys Asn Met Glu Thr Gly Glu Thr Cys Val Tyr Pro
305                 310                 315                 320

```
Thr Gln Pro Ser Val Ala Gln Lys Asn Trp Tyr Ile Ser Lys Asn Pro
                325                 330                 335

Lys Asp Lys Arg His Val Trp Phe Gly Glu Ser Met Thr Asp Gly Phe
            340                 345                 350

Gln Phe Glu Tyr Gly Gly Gln Gly Ser Asp Pro Ala Asp Val Ala Ile
        355                 360                 365

Gln Leu Thr Phe Leu Arg Leu Met Ser Thr Glu Ala Ser Gln Asn Ile
    370                 375                 380

Thr Tyr His Cys Lys Asn Ser Val Ala Tyr Met Asp Gln Gln Thr Gly
385                 390                 395                 400

Asn Leu Lys Lys Ala Leu Leu Leu Lys Gly Ser Asn Glu Ile Glu Ile
                405                 410                 415

Arg Ala Glu Gly Asn Ser Arg Phe Thr Tyr Ser Val Thr Val Asp Gly
            420                 425                 430

Cys Thr Ser His Thr Gly Ala Trp Gly Lys Thr Val Ile Glu Tyr Lys
        435                 440                 445

Thr Thr Lys Ser Ser Arg Leu Pro Ile Ile Asp Val Ala Pro Leu Asp
    450                 455                 460

Val Gly Ala Pro Asp Gln Glu Phe Gly Phe Asp Val Gly Pro Val Cys
465                 470                 475                 480

Phe Leu

<210> SEQ ID NO 3
<211> LENGTH: 495
<212> TYPE: PRT
<213> ORGANISM: ARTIFICIAL SEQUENCE
<220> FEATURE:
<223> OTHER INFORMATION: FUSION PROTEIN

<400> SEQUENCE: 3

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
            85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Ser Asn Gly Leu Pro Gly Pro
            180                 185                 190

Ile Gly Pro Pro Gly Pro Arg Gly Arg Thr Gly Asp Ala Gly Pro Val
```

```
            195                 200                 205
Gly Pro Pro Gly Pro Pro Gly Pro Pro Gly Pro Pro Ser
210                 215                 220
Ala Gly Phe Asp Phe Ser Phe Leu Pro Gln Pro Gln Glu Lys Ala
225                 230                 235                 240
His Asp Gly Gly Arg Tyr Tyr Arg Ala Asn Asp Ala Asn Val Val Arg
                245                 250                 255
Asp Arg Asp Leu Glu Val Asp Thr Thr Leu Lys Ser Leu Ser Gln Gln
                260                 265                 270
Ile Glu Asn Ile Arg Ser Pro Glu Gly Ser Arg Lys Asn Pro Ala Arg
                275                 280                 285
Thr Cys Arg Asp Leu Lys Met Cys His Ser Asp Trp Lys Ser Gly Glu
290                 295                 300
Tyr Trp Ile Asp Pro Asn Gln Gly Cys Asn Leu Asp Ala Ile Lys Val
305                 310                 315                 320
Phe Cys Asn Met Glu Thr Gly Glu Thr Cys Val Tyr Pro Thr Gln Pro
                325                 330                 335
Ser Val Ala Gln Lys Asn Trp Tyr Ile Ser Lys Asn Pro Lys Asp Lys
                340                 345                 350
Arg His Val Trp Phe Gly Glu Ser Met Thr Asp Gly Phe Gln Phe Glu
                355                 360                 365
Tyr Gly Gly Gln Gly Ser Asp Pro Ala Asp Val Ala Ile Gln Leu Thr
370                 375                 380
Phe Leu Arg Leu Met Ser Thr Glu Ala Ser Gln Asn Ile Thr Tyr His
385                 390                 395                 400
Cys Lys Asn Ser Val Ala Tyr Met Asp Gln Gln Thr Gly Asn Leu Lys
                405                 410                 415
Lys Ala Leu Leu Leu Lys Gly Ser Asn Glu Ile Glu Ile Arg Ala Glu
                420                 425                 430
Gly Asn Ser Arg Phe Thr Tyr Ser Val Thr Val Asp Gly Cys Thr Ser
                435                 440                 445
His Thr Gly Ala Trp Gly Lys Thr Val Ile Glu Tyr Lys Thr Thr Lys
450                 455                 460
Ser Ser Arg Leu Pro Ile Ile Asp Val Ala Pro Leu Asp Val Gly Ala
465                 470                 475                 480
Pro Asp Gln Glu Phe Gly Phe Asp Val Gly Pro Val Cys Phe Leu
                485                 490                 495

<210> SEQ ID NO 4
<211> LENGTH: 498
<212> TYPE: PRT
<213> ORGANISM: Artificial
<220> FEATURE:
<223> OTHER INFORMATION: Fusion protein

<400> SEQUENCE: 4

Leu Pro Ala Arg Glu Gly Pro Glu Leu Ser Pro Asp Asp Pro Ala Gly
1               5                   10                  15
Leu Leu Asp Leu Arg Gln Gly Met Phe Ala Gln Leu Val Ala Gln Asn
                20                  25                  30
Val Leu Leu Ile Asp Gly Pro Leu Ser Trp Tyr Ser Asp Pro Gly Leu
                35                  40                  45
Ala Gly Val Ser Leu Thr Gly Gly Leu Ser Tyr Lys Glu Asp Thr Lys
            50                  55                  60
Glu Leu Val Val Ala Lys Ala Gly Val Tyr Tyr Val Phe Phe Gln Leu
```

```
            65                  70                  75                  80
        Glu Leu Arg Arg Val Ala Gly Glu Gly Ser Gly Ser Val Ser Leu
                        85                  90                  95
        Ala Leu His Leu Gln Pro Leu Arg Ser Ala Gly Ala Ala Ala Leu
                        100                 105                 110
        Ala Leu Thr Val Asp Leu Pro Ala Ser Ser Glu Ala Arg Asn Ser
                        115                 120                 125
        Ala Phe Gly Phe Gln Gly Arg Leu Leu His Leu Ser Ala Gly Gln Arg
                    130                 135                 140
        Leu Gly Val His Leu His Thr Glu Ala Arg Ala Arg His Ala Trp Gln
        145                 150                 155                 160
        Leu Thr Gln Gly Ala Thr Val Leu Gly Leu Phe Arg Val Thr Pro Glu
                        165                 170                 175
        Ile Pro Ala Gly Leu Pro Ser Pro Arg Ser Glu Gly Ser Asn Gly Leu
                        180                 185                 190
        Pro Gly Pro Ile Gly Pro Pro Gly Pro Arg Gly Arg Thr Gly Asp Ala
                        195                 200                 205
        Gly Pro Val Gly Pro Pro Gly Pro Pro Gly Pro Pro Gly Pro Pro Gly
                    210                 215                 220
        Pro Pro Ser Ala Gly Phe Asp Phe Ser Phe Leu Pro Gln Pro Pro Gln
        225                 230                 235                 240
        Glu Lys Ala His Asp Gly Gly Arg Tyr Tyr Arg Ala Asn Asp Ala Asn
                        245                 250                 255
        Val Val Arg Asp Arg Asp Leu Glu Val Asp Thr Thr Leu Lys Ser Leu
                        260                 265                 270
        Ser Gln Gln Ile Glu Asn Ile Arg Ser Pro Glu Gly Ser Arg Lys Asn
                        275                 280                 285
        Pro Ala Arg Thr Cys Arg Asp Leu Lys Met Cys His Ser Asp Trp Lys
                        290                 295                 300
        Ser Gly Glu Tyr Trp Ile Asp Pro Asn Gln Gly Cys Asn Leu Asp Ala
        305                 310                 315                 320
        Ile Lys Val Phe Cys Asn Met Glu Thr Gly Glu Thr Cys Val Tyr Pro
                        325                 330                 335
        Thr Gln Pro Ser Val Ala Gln Lys Asn Trp Tyr Ile Ser Lys Asn Pro
                        340                 345                 350
        Lys Asp Lys Arg His Val Trp Phe Gly Glu Ser Met Thr Asp Gly Phe
                        355                 360                 365
        Gln Phe Glu Tyr Gly Gly Gln Gly Ser Asp Pro Ala Asp Val Ala Ile
                        370                 375                 380
        Gln Leu Thr Phe Leu Arg Leu Met Ser Thr Glu Ala Ser Gln Asn Ile
        385                 390                 395                 400
        Thr Tyr His Cys Lys Asn Ser Val Ala Tyr Met Asp Gln Gln Thr Gly
                        405                 410                 415
        Asn Leu Lys Lys Ala Leu Leu Leu Lys Gly Ser Asn Glu Ile Glu Ile
                        420                 425                 430
        Arg Ala Glu Gly Asn Ser Arg Phe Thr Tyr Ser Val Thr Val Asp Gly
                        435                 440                 445
        Cys Thr Ser His Thr Gly Ala Trp Gly Lys Thr Val Ile Glu Tyr Lys
                        450                 455                 460
        Thr Thr Lys Ser Ser Arg Leu Pro Ile Ile Asp Val Ala Pro Leu Asp
        465                 470                 475                 480
        Val Gly Ala Pro Asp Gln Glu Phe Gly Phe Asp Val Gly Pro Val Cys
                        485                 490                 495
```

Phe Leu

<210> SEQ ID NO 5
<211> LENGTH: 443
<212> TYPE: PRT
<213> ORGANISM: ARTIFICIAL SEQUENCE
<220> FEATURE:
<223> OTHER INFORMATION: FUSION PROTEIN

<400> SEQUENCE: 5

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu Gly Ser Asn Gly Leu Pro Gly Pro Ile Gly Pro
    130                 135                 140

Pro Gly Pro Arg Gly Arg Thr Gly Asp Ala Gly Pro Val Gly Pro Pro
145                 150                 155                 160

Gly Pro Pro Gly Pro Pro Gly Pro Pro Gly Pro Pro Ser Ala Gly Phe
                165                 170                 175

Asp Phe Ser Phe Leu Pro Gln Pro Pro Gln Glu Lys Ala His Asp Gly
            180                 185                 190

Gly Arg Tyr Tyr Arg Ala Asn Asp Ala Asn Val Val Arg Asp Arg Asp
        195                 200                 205

Leu Glu Val Asp Thr Thr Leu Lys Ser Leu Ser Gln Gln Ile Glu Asn
    210                 215                 220

Ile Arg Ser Pro Glu Gly Ser Arg Lys Asn Pro Ala Arg Thr Cys Arg
225                 230                 235                 240

Asp Leu Lys Met Cys His Ser Asp Trp Lys Ser Gly Glu Tyr Trp Ile
                245                 250                 255

Asp Pro Asn Gln Gly Cys Asn Leu Asp Ala Ile Lys Val Phe Cys Asn
            260                 265                 270

Met Glu Thr Gly Glu Thr Cys Val Tyr Pro Thr Gln Pro Ser Val Ala
        275                 280                 285

Gln Lys Asn Trp Tyr Ile Ser Lys Asn Pro Lys Asp Lys Arg His Val
    290                 295                 300

Trp Phe Gly Glu Ser Met Thr Asp Gly Phe Gln Phe Glu Tyr Gly Gly
305                 310                 315                 320

Gln Gly Ser Asp Pro Ala Asp Val Ala Ile Gln Leu Thr Phe Leu Arg
                325                 330                 335

Leu Met Ser Thr Glu Ala Ser Gln Asn Ile Thr Tyr His Cys Lys Asn
            340                 345                 350

```
Ser Val Ala Tyr Met Asp Gln Gln Thr Gly Asn Leu Lys Lys Ala Leu
            355                 360                 365

Leu Leu Lys Gly Ser Asn Glu Ile Glu Ile Arg Ala Glu Gly Asn Ser
370                 375                 380

Arg Phe Thr Tyr Ser Val Thr Val Asp Gly Cys Thr Ser His Thr Gly
385                 390                 395                 400

Ala Trp Gly Lys Thr Val Ile Glu Tyr Lys Thr Thr Lys Ser Ser Arg
            405                 410                 415

Leu Pro Ile Ile Asp Val Ala Pro Leu Asp Val Gly Ala Pro Asp Gln
                420                 425                 430

Glu Phe Gly Phe Asp Val Gly Pro Val Cys Phe
            435                 440
```

<210> SEQ ID NO 6
<211> LENGTH: 447
<212> TYPE: PRT
<213> ORGANISM: Artificial
<220> FEATURE:
<223> OTHER INFORMATION: Fusion protein

<400> SEQUENCE: 6

```
Leu Pro Ala Gln Val Ser His Arg Tyr Pro Arg Ile Gln Ser Ile Lys
1               5                   10                  15

Val Gln Phe Thr Glu Tyr Lys Lys Glu Lys Gly Phe Ile Leu Thr Ser
            20                  25                  30

Gln Lys Glu Asp Glu Ile Met Lys Val Gln Asn Asn Ser Val Ile Ile
        35                  40                  45

Asn Cys Asp Gly Phe Tyr Leu Ile Ser Leu Lys Gly Tyr Phe Ser Gln
50                  55                  60

Glu Val Asn Ile Ser Leu His Tyr Gln Lys Asp Glu Glu Pro Leu Phe
65                  70                  75                  80

Gln Leu Lys Lys Val Arg Ser Val Asn Ser Leu Met Val Ala Ser Leu
                85                  90                  95

Thr Tyr Lys Asp Lys Val Tyr Leu Asn Val Thr Thr Asp Asn Thr Ser
            100                 105                 110

Leu Asp Asp Phe His Val Asn Gly Gly Glu Leu Ile Leu Ile His Gln
        115                 120                 125

Asn Pro Gly Glu Phe Cys Val Leu Gly Ser Asn Gly Leu Pro Gly Pro
130                 135                 140

Ile Gly Pro Pro Gly Pro Arg Gly Arg Thr Gly Asp Ala Gly Pro Val
145                 150                 155                 160

Gly Pro Pro Gly Pro Pro Gly Pro Pro Gly Pro Pro Gly Pro Pro Ser
                165                 170                 175

Ala Gly Phe Asp Phe Ser Phe Leu Pro Gln Pro Pro Gln Glu Lys Ala
            180                 185                 190

His Asp Gly Gly Arg Tyr Tyr Arg Ala Asn Asp Ala Asn Val Val Arg
        195                 200                 205

Asp Arg Asp Leu Glu Val Asp Thr Thr Leu Lys Ser Leu Ser Gln Gln
210                 215                 220

Ile Glu Asn Ile Arg Ser Pro Glu Gly Ser Arg Lys Asn Pro Ala Arg
225                 230                 235                 240

Thr Cys Arg Asp Leu Lys Met Cys His Ser Asp Trp Lys Ser Gly Glu
                245                 250                 255

Tyr Trp Ile Asp Pro Asn Gln Gly Cys Asn Leu Asp Ala Ile Lys Val
            260                 265                 270
```

```
Phe Cys Asn Met Glu Thr Gly Glu Thr Cys Val Tyr Pro Thr Gln Pro
            275                 280                 285

Ser Val Ala Gln Lys Asn Trp Tyr Ile Ser Lys Asn Pro Lys Asp Lys
        290                 295                 300

Arg His Val Trp Phe Gly Ser Met Thr Asp Gly Phe Gln Phe Glu
305                 310                 315                 320

Tyr Gly Gly Gln Gly Ser Asp Pro Ala Asp Val Ala Ile Gln Leu Thr
                325                 330                 335

Phe Leu Arg Leu Met Ser Thr Glu Ala Ser Gln Asn Ile Thr Tyr His
            340                 345                 350

Cys Lys Asn Ser Val Ala Tyr Met Asp Gln Gln Thr Gly Asn Leu Lys
            355                 360                 365

Lys Ala Leu Leu Leu Lys Gly Ser Asn Glu Ile Glu Ile Arg Ala Glu
        370                 375                 380

Gly Asn Ser Arg Phe Thr Tyr Ser Val Thr Val Asp Gly Cys Thr Ser
385                 390                 395                 400

His Thr Gly Ala Trp Gly Lys Thr Val Ile Glu Tyr Lys Thr Thr Lys
                405                 410                 415

Ser Ser Arg Leu Pro Ile Ile Asp Val Ala Pro Leu Asp Val Gly Ala
            420                 425                 430

Pro Asp Gln Glu Phe Gly Phe Asp Val Gly Pro Val Cys Phe Leu
            435                 440                 445

<210> SEQ ID NO 7
<211> LENGTH: 402
<212> TYPE: PRT
<213> ORGANISM: ARTIFICIAL SEQUENCE
<220> FEATURE:
<223> OTHER INFORMATION: FUSION PROTEIN

<400> SEQUENCE: 7

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
130                 135                 140

Gly Glu Ser Gly Gln Val Tyr Phe Gly Ile Ile Ala Leu Arg Ser Glu
145                 150                 155                 160

Pro Met Asp Phe Lys Ile Asn Thr Asp Glu Ile Met Thr Ser Leu Lys
                165                 170                 175

Ser Val Asn Gly Gln Ile Glu Ser Leu Ile Ser Pro Asp Gly Ser Arg
            180                 185                 190
```

-continued

```
Lys Asn Pro Ala Arg Asn Cys Arg Asp Leu Lys Phe Cys His Pro Glu
        195                 200                 205

Leu Lys Ser Gly Glu Tyr Trp Val Asp Pro Asn Gln Gly Cys Lys Leu
    210                 215                 220

Asp Ala Ile Lys Val Phe Cys Asn Met Glu Thr Gly Glu Thr Cys Ile
225                 230                 235                 240

Ser Ala Asn Pro Leu Asn Val Pro Arg Lys His Trp Trp Thr Asp Ser
                245                 250                 255

Ser Ala Glu Lys Lys His Val Trp Phe Gly Glu Ser Met Asp Gly Gly
            260                 265                 270

Phe Gln Phe Ser Tyr Gly Asn Pro Glu Leu Pro Glu Asp Val Leu Asp
        275                 280                 285

Val Gln Leu Ala Phe Leu Arg Leu Leu Ser Ser Arg Ala Ser Gln Asn
    290                 295                 300

Ile Thr Tyr His Cys Lys Asn Ser Ile Ala Tyr Met Asp Gln Ala Ser
305                 310                 315                 320

Gly Asn Val Lys Lys Ala Leu Lys Leu Met Gly Ser Asn Glu Gly Glu
                325                 330                 335

Phe Lys Ala Glu Gly Asn Ser Lys Phe Thr Tyr Thr Val Leu Glu Asp
            340                 345                 350

Gly Cys Thr Lys His Thr Gly Glu Trp Ser Lys Thr Val Phe Glu Tyr
        355                 360                 365

Arg Thr Arg Lys Ala Val Arg Leu Pro Ile Val Asp Ile Ala Pro Tyr
    370                 375                 380

Asp Ile Gly Gly Pro Asp Gln Glu Phe Gly Val Asp Val Gly Pro Val
385                 390                 395                 400

Cys Phe
```